US012098195B2

(12) United States Patent
Liu et al.

(10) Patent No.: US 12,098,195 B2
(45) Date of Patent: Sep. 24, 2024

(54) ANTI-IL-23P19 ANTIBODY AND USE THEREOF IN TREATING DISEASES

(71) Applicant: INNOVENT BIOLOGICS (SUZHOU) CO., LTD., Jiangsu (CN)

(72) Inventors: Junjian Liu, Jiangsu (CN); Min Wu, Jiangsu (CN); Li Li, Jiangsu (CN); Shuaixiang Zhou, Jiangsu (CN); Enkun Zhou, Jiangsu (CN)

(73) Assignee: INNOVENT BIOLOGICS (SUZHOU) CO., LTD., Jiangsu (CN)

( * ) Notice: Subject to any disclaimer, the term of this patent is extended or adjusted under 35 U.S.C. 154(b) by 775 days.

(21) Appl. No.: 17/253,207

(22) PCT Filed: Nov. 27, 2019

(86) PCT No.: PCT/CN2019/121261
§ 371 (c)(1),
(2) Date: Dec. 17, 2020

(87) PCT Pub. No.: WO2020/108530
PCT Pub. Date: Jun. 4, 2020

(65) Prior Publication Data
US 2021/0115130 A1    Apr. 22, 2021

(30) Foreign Application Priority Data

Nov. 27, 2018    (CN) .................. 201811424552.X

(51) Int. Cl.
| | | |
|---|---|---|
| C07K 16/24 | (2006.01) | |
| A61K 39/395 | (2006.01) | |
| A61K 47/68 | (2017.01) | |
| A61P 37/06 | (2006.01) | |
| G01N 33/564 | (2006.01) | |
| A61K 39/00 | (2006.01) | |
| A61K 45/06 | (2006.01) | |

(52) U.S. Cl.
CPC ........ *C07K 16/244* (2013.01); *A61K 39/3955* (2013.01); *A61K 47/6845* (2017.08); *A61P 37/06* (2018.01); *G01N 33/564* (2013.01); *A61K 2039/505* (2013.01); *A61K 45/06* (2013.01); *C07K 2317/24* (2013.01); *C07K 2317/31* (2013.01); *C07K 2317/565* (2013.01); *C07K 2317/732* (2013.01); *C07K 2317/76* (2013.01); *C07K 2317/92* (2013.01)

(58) Field of Classification Search
CPC ............ C07K 16/244; C07K 2317/565; A61K 39/3995; A61P 37/06
See application file for complete search history.

(56) References Cited

U.S. PATENT DOCUMENTS

| | | | |
|---|---|---|---|
| 6,171,586 B1 | 1/2001 | Lam et al. | |
| 7,083,784 B2 | 8/2006 | Dall'Acqua et al. | |
| 7,658,921 B2 | 2/2010 | Dall'Acqua et al. | |
| 7,670,600 B2 | 3/2010 | Dall'Acqua et al. | |
| 7,704,497 B2 | 4/2010 | Dall'Acqua et al. | |
| 8,012,476 B2 | 9/2011 | Dall'Acqua et al. | |
| 8,323,962 B2 | 12/2012 | Dall'Acqua et al. | |
| 8,475,792 B2 | 7/2013 | Dall'Acqua et al. | |
| 8,513,389 B2 | 8/2013 | Presta et al. | |
| 8,795,661 B2 | 8/2014 | Dall'Acqua et al. | |
| 9,562,100 B2 | 2/2017 | Dall'Acqua et al. | |
| 9,718,884 B2 | 8/2017 | Millican, Jr. et al. | |
| 2007/0009526 A1 | 1/2007 | Benson et al. | |
| 2010/0111966 A1 | 5/2010 | Presta et al. | |
| 2013/0315911 A1 | 11/2013 | Stevens et al. | |
| 2014/0086931 A1 | 3/2014 | Krause et al. | |
| 2014/0178401 A1 | 6/2014 | Nabozny et al. | |
| 2015/0329632 A1 | 11/2015 | Kashi et al. | |
| 2016/0237151 A1 | 8/2016 | Benson et al. | |
| 2018/0008707 A1 | 1/2018 | Bussemer et al. | |
| 2018/0134784 A1 | 5/2018 | Fitzgerald et al. | |

FOREIGN PATENT DOCUMENTS

| | | |
|---|---|---|
| CN | 101252951 A | 8/2008 |
| CN | 101389351 A | 3/2009 |
| CN | 101687925 A | 3/2010 |
| CN | 102202655 B | 9/2011 |
| CN | 103396489 A | 11/2013 |
| CN | 102887954 B | 2/2015 |
| CN | 104507497 A | 4/2015 |
| CN | 104870016 A | 8/2015 |
| CN | 107635581 A | 1/2018 |
| CN | 108064249 A | 5/2018 |
| CN | 109206516 A | 1/2019 |

(Continued)

OTHER PUBLICATIONS

Benjamini et al, 1991. Immunology: A Short Course, 2nd edition, p. 40 only.*
Ferrara et al (2015. mAbs. 7(1): 32-41).*
Singh et al: Selective targeting of the IL23 pathway: Generation and characterization of a novel high-affinity humanized anti-IL23A antibody; mAbs, 2015, 7:4, 778-791.
Oppmann, et al. "Novel p19 Protein Engages IL-12p40 to Form a Cytokine, IL-23, with Biological Activities Similar as Well as Distinct from IL-12", (2000) Immunity, 13:715-725.
Wiekowski, et al. "Ubiquitous Transgenic Expression of the IL-23 Subunit p19 Induces Multiorgan Inflammation, Runting, Infertility, and Premature Death", (2001) J. Immunol. 166:7563-7570.

(Continued)

*Primary Examiner* — Zachary C Howard
(74) *Attorney, Agent, or Firm* — Leason Ellis LLP

(57) ABSTRACT

The present invention relates to a novel antibody and an antibody fragment thereof that specifically bind to IL-23p19 and a composition comprising the antibody or the antibody fragment thereof. In addition, the present invention relates to a nucleic acid encoding the antibody or the antibody fragment thereof, a host cell comprising the nucleic acid, and related use. Furthermore, the present invention relates to therapeutic and diagnostic use of the antibody and the antibody fragment.

27 Claims, 2 Drawing Sheets

Specification includes a Sequence Listing.

(56) References Cited

FOREIGN PATENT DOCUMENTS

| | | |
|---|---|---|
| EP | 1355919 B1 | 11/2010 |
| EP | 2341060 A1 | 7/2011 |
| EP | 2354149 A1 | 8/2011 |
| EP | 3326649 A1 | 5/2018 |
| JP | 2010-518856 | 6/2010 |
| WO | 2006/044908 A2 | 4/2006 |
| WO | 2006/050166 A2 | 5/2006 |
| WO | 2007/005955 A2 | 1/2007 |
| WO | 2007/075624 A1 | 7/2007 |
| WO | 2007/076524 A2 | 7/2007 |
| WO | 2008/103432 A1 | 8/2008 |
| WO | 2008/103473 A1 | 8/2008 |
| WO | 2010/027766 A1 | 3/2010 |
| WO | 2011/161226 A2 | 12/2011 |
| WO | 2013/165791 A1 | 11/2013 |
| WO | 2018/093841 A1 | 5/2018 |

OTHER PUBLICATIONS

Parham, et al. "A Receptor for the Heterodimeric Cytokine IL-23 is Composed of IL-12Rβ1 and a Novel Cytokine Receptor Subunit, IL-23R", (2002) J. Immunol. 168:5699-5708.
Frucht, D. "IL-23: A Cytokine That Acts on Memory T Cells", (2002) Sci STKE 2002, E1-E3.
Elkins, et al. "In Vivo Clearance of an Intracellular Bacterium, *Francisella tularensis* LVS, is Dependent on the p40 Subunit of Interleukin-12 (IL-12) but Not on IL-12 p70", (2002) Infection Immunity 70:1936-1948.
Robbie, et al., A Novel Investigational Fc-Modified Humanized Monoclonal Antibody, Motavizumab-YTE, Has an Extended Half-Life in Healthy Adults, Antimicrobial Agents and Chemotherapy, 2013, 57(12): p. 6147-6153.
Cua, et al. "Interleukin-23 rather than interleukin-12 is the critical cytokine for autoimmune inflammation of the brain", (2003) Nature 421:744-748.
Murphy et al. Divergent pro- and antiinflammatory roles for IL-23 and IL-12 in joint autoimmune inflammation. J Exp Med (2003) 198: 1951-1957.
Bravo and Heath, Receptor Recognition by gp130 Cytokines, Embo J. (2000) 19(11):2399-2411.
Tang, et al., "Interleukin-23: as a drug target for autoimmune inflammatory diseases", Immunology, 135(2), p. 112-124, 2012.
Izcue et al., "Interleukin-23 Restrains Regulatory T Cell Activity to Drive T Cell-Dependent Colitis", Immunity, 28(4), p. 559-570, 2008.
Savvatis et al., "Interleukin-23 Deficiency Leads to Impaired Wound Healing and Adverse Prognosis After Myocardial Infarction", Circulation: Heart Failure, 7(1), pp. 161-171, 2014.
U.S. Appl. No. 61/642,032.
International Search Report and Written Opinion of PCT/CN201919/121261, mailed Mar. 4, 2020.
The State Food and Drug Administration Technical Guidelines for Stability Research of Biological Products, issued on Apr. 15, 2015.
European Medicines Agency, ICH Q1A (R2), Stability Testing of New Drug Substances and Products, Aug. 2003.
Specification and Drawings of U.S. Appl. No. 17/924,214.
International Search Report and Written Opinion of PCT/CN2021/093219, mailed Aug. 16, 2021.
Sheng et al.: "Aberrant expression of IL-23/IL-23R in patients with breast cancer and its clinical significance", Molecular Medicine Reports, 2018, vol. 17, Issue 3: 4639-4644.
Du et al.: "Molecular Basis of Recognition of Human Osteopontin by 23C3, a Potential Therapeutic Antibody for Treatment of Rheumatoid Arthritis", J. Mol. Biol., 2008; 382(4): 835-842. [8 pages].
Caldas et al.: "Humanization of the anti-CD18 antibody 6.7: an unexpected effect of a framework residue in binding to antigen", Molecular Immunology, 2003; 39(15): 941-952. [12 pages].
Casadevall et al.: "Immunoglobulin isotype influences affinity and specificity", PNAS, 2012, vol. 109, No. 31, p. 12272-12273. [2 pages].
Kunik et al.: "Structural Consensus among Antibodies Defines the Antigen Binding Site", PLOS Computational Biology, 2021, vol. 8; Issue 2, p. e1002388 [12 pages].

* cited by examiner

ANTI-IL-23P19 ANTIBODY AND USE THEREOF IN TREATING DISEASES

The present invention relates to a novel antibody and an antibody fragment thereof that specifically bind to IL-23p19 and a composition comprising the antibody or the antibody fragment thereof. In addition, the present invention relates to a nucleic acid encoding the antibody or the antibody fragment thereof, a host cell comprising the nucleic acid, and related use. Furthermore, the present invention relates to therapeutic and diagnostic use of the antibody and the antibody fragment.

BACKGROUND

Interleukin (IL)-12 is a secreted heterodimeric cytokine consisting of two disulfide-linked glycosylated subunits, which are named p35 and p40 after their approximate molecular weights. It has been found that the p40 subunit of IL-12 can also be linked to an isolated protein subunit named p19 to form a new cytokine, interleukin-23 (IL-23) (Oppman et al., 2000).

Interleukin-23 (IL-23) is a heterodimeric cytokine comprising the following two subunits: a p19 specific to IL-23 (IL-23p19) and a p40 shared with IL-12 (IL-12) (IL-12p40). The p19 subunit is structurally related to IL-6, granulocyte colony stimulating factor (G-CSF) and p35 subunit of IL-12. IL-23 mediates signaling by binding to a heterodimeric receptor comprising two subunits, which are IL-23R specific to the IL-23 receptor and IL-12Rb1 shared with the IL-12 receptor.

Many previous studies have demonstrated that the consequences of genetic defects in p40 (p40 knockout mice; p40KO mice) are more serious than those observed in p35-deficient mice (e.g., p35KO mice). These results are generally interpreted as p40 knockout not only blocking IL-12 expression, but also IL-23 expression. See, for example, Oppmann et al. (2000) *Immunity* 13:715-725; Wiekowski et al. (2001) *J. Immunol.* 166:7563-7570; Parham et al. (2002) *J. Immunol.* 168:5699-708; Frucht (2002) Sci STKE 2002, E1-E3; Elkins et al. (2002) *Infection Immunity* 70:1936-1948. Recent studies have demonstrated that IL-23 inhibition in IL-23p19-deficient mice or by IL-23-specific antibody neutralization can provide benefits comparable to anti-IL-12p40 strategies (Cua et al., 2003; Murphy et al., 2003; Benson et al., 2004). Therefore, increased specificity of IL-23 in immune-mediated diseases is evident. IL-23 neutralization does not inhibit IL-12 pathway and thus can provide effective treatment for immune-mediated diseases, while having limited effect on important host immune defense mechanisms. This will represent a significant improvement over current treatment options.

Therefore, the present invention focuses on developing a novel IL-23p19 antibody comparable or superior to existing antibodies, in order to meet the need for a novel IL-23P19 antibody in the art.

SUMMARY

The present invention provides a novel antibody binding to IL-23p19, and an antigen-binding fragment thereof.

In some embodiments, the anti-IL-23p19 antibody of the present invention has one or more of the following properties:
(i) binding to IL-23p19 with high affinity;
(ii) blocking IL-23 signaling pathway, e.g., by blocking IL-23 induction of IL-17 secretion in cells; and
(iii) treating or preventing IL-23-associated diseases.

In some embodiments, the present invention provides an antibody binding to IL-23p19 or an antigen-binding fragment thereof, comprising 3 heavy chain CDRs (HCDRs) of the sequence set forth in SEQ ID NO: 9 or 10, and/or 3 light chain CDRs (LCDRs) of the sequence set forth in SEQ ID NO: 11 or 12.

In some embodiments, the present invention provides a nucleic acid encoding the antibody or the fragment thereof disclosed herein, a vector comprising the nucleic acid, and a host cell comprising the vector.

In some embodiments, the present invention provides a method for preparing the antibody or the fragment thereof disclosed herein.

In some embodiments, the present invention provides an immunoconjugate, a pharmaceutical composition, and a combination product comprising the antibody disclosed herein.

The present invention further provides a method for blocking IL-23 mediated signaling pathways in a subject, and a method for preventing or treating IL-23-associated diseases, e.g., immune system diseases (such as autoimmune diseases or inflammation) using the antibody disclosed herein.

The present invention also relates to a method for detecting IL-23p19 in a sample.

The present invention is further illustrated in the following drawings and specific embodiments. However, these drawings and specific embodiments should not be construed as limiting the scope of the present invention, and modifications easily conceived by those skilled in the art will be included in the spirit of the present invention and the protection scope of the appended claims.

DETAILED DESCRIPTION

I. Definitions

Figure 1:
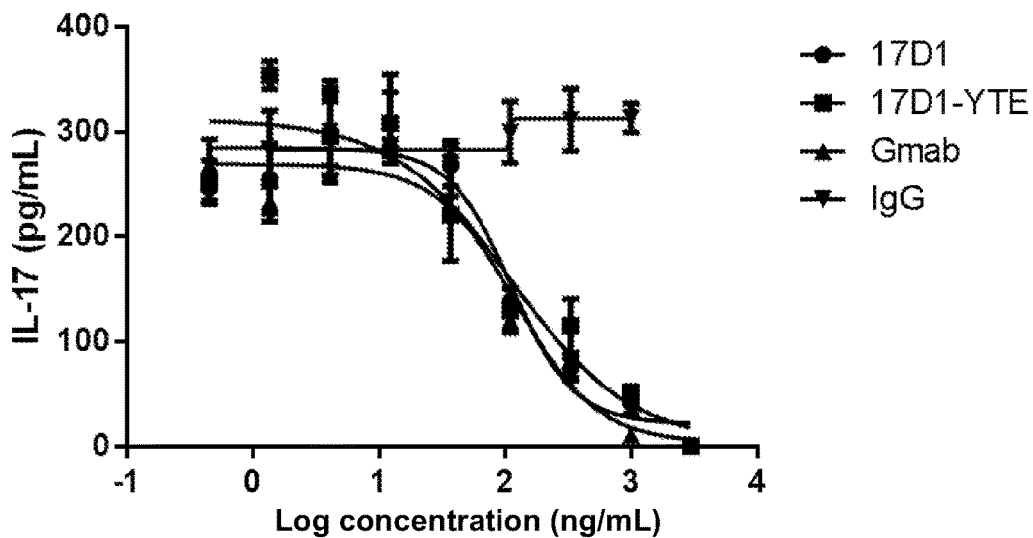
FIG. 1 shows the inhibited IL-23-induced IL-17 secretion by humanized antibodies 17D1 and 17D1-YTE in mouse splenic lymphocytes.

Before the present invention is described in detail below, it should be understood that the present invention is not limited to the particular methodology, protocols, and reagents described herein, as these may vary. It should also be understood that the terminology used herein is only intended to describe specific embodiments rather than limit the scope of the present invention, which will be limited only by the appended claims. Unless otherwise defined, any technical and scientific term used herein has the same meaning as commonly understood by those of ordinary skill in the art to which the present invention belongs.

For the purpose of explaining this specification, the following definitions will be used, and wherever appropriate, terms used in the singular form may also include the plural form, and vice versa. It should be understood that the terminology used herein is for the purpose of describing specific embodiments only, and is not intended to be limiting.

The term "about" used in combination with a numerical value is intended to encompass the numerical values in a range from a lower limit less than the specified numerical value by 5% to an upper limit greater than the specified numerical value by 5%.

As used herein, the term "and/or" refers to any one of the options or any two or more of the options.

As used herein, the term "comprise" or "include" is intended to mean that the described elements, integers or steps are included, but not to the exclusion of any other elements, integers or steps. The term "comprise" or "include" used herein, unless otherwise specified, also encompasses the situation where the entirety consists of the described elements, integers or steps. For example, when referring to "comprise" an antibody variable region of a particular sequence, it is also intended to encompass an antibody variable region consisting of the specific sequence.

The p19 subunit of IL-23 (also referred to herein as "IL-23p19" or "p19 subunit") is a polypeptide having 189 amino acids, comprising a leader sequence of 21 amino acids (Oppmann et al., Immunity 13:715 (2000); SEQ ID NO: 181), and 4 packed alpha helices of A, B, C, and D, with an up-up-down-down topology. The 4 helices are linked by 3 polypeptide loops. A-B and C-D loops are relatively long as they link parallel helices. The short B-C loop links the B and C helices in reverse parallel. The p19 subunit of IL-23 is a member of the IL-6 family of helical cytokines. The cytokine family members bind to cognate receptors through three conserved epitopes (sites I, II, and III; Bravo and Heath (2000) EMBO J., 19:2399-2411). The p19 subunit interacts with 3 cytokine receptor subunits to form a competent signaling complex. When expressed in cells, the p19 subunit first forms a complex with the p40 subunit, and the p19 subunit shares the p40 subunit with IL-12. The p19p40 complex is secreted from cells as a heterodimeric protein and is referred to as IL-23. In one embodiment, the IL-23p19 disclosed herein is derived from human (NCBI: AAG37232) or cynomolgus monkey (NCBI: AEY84629).

The term "anti-IL-23p19 antibody", "anti-IL-23p19", "IL-23p19 antibody" or "antibody binding to IL-23p19" as used herein refers to an antibody which can bind to human or cynomolgus monkey IL-23p19 subunit or fragment thereof with sufficient affinity so as to serve as a diagnostic agent and/or a therapeutic agent targeting human or cynomolgus monkey IL-23p19. In one embodiment, the anti-IL-23p19 antibody binds to a non-human or -cynomolgus monkey IL-23p19 protein to an extent less than about 10%, about 20%, about 30%, about 40%, about 50%, about 60%, about 70%, about 80%, or about 90% or more of the binding of the antibody to human or cynomolgus monkey IL-23p19, as measured, for example, by radioimmunoassay (RIA), biological optical interferometry, or MSD assay.

"Antibody fragment" refers to a molecule different from an intact antibody, which comprises a portion of the intact antibody and binds to an antigen to which the intact antibody binds. Examples of the antibody fragment include but are not limited to Fv, Fab, Fab', Fab'-SH, F(ab')$_2$; a diabody; a linear antibody; a single-chain variable fragment (e.g., scFv); a single-domain antibody; a bivalent or bispecific antibody or a fragment thereof; a Camelidae antibody; and a bispecific antibody or multispecific antibody formed from antibody fragments.

As used herein, the term "epitope" refers to a moiety of an antigen (e.g., IL-23p19) that interacts with an antibody molecule.

"Antibody that binds to the same or overlapping epitope" as a reference antibody refers to an antibody that blocks more than 50%, 60%, 70%, 80%, 90%, or 95% of the binding of the reference antibody to its antigen in a competition assay, or conversely, the reference antibody blocking more than 50%, 60%, 70%, 80%, 90%, or 95% of the binding of the antibody to its antigen in a competition assay.

An antibody that competes with a reference antibody to bind to its antigen refers to an antibody that blocks more than 50%, 60%, 70%, 80%, 90%, or 95% of the binding of the reference antibody to its antigen in a competition assay. Conversely, the reference antibody blocks more than 50%, 60%, 70%, 80%, 90%, or 95% of the binding of the antibody to its antigen in a competition assay. Numerous types of competitive binding assays can be used to determine whether an antibody competes with another, such as direct or indirect solid-phase radioimmunoassay (RIA), direct or indirect solid-phase enzyme immunoassay (EIA), and sandwich competition assay (see, e.g., Stahli et al., 1983, *Methods in Enzymology* 9: 242-253).

An antibody that inhibits (e.g., competitively inhibits) the binding of a reference antibody to its antigen refers to an antibody that inhibits more than 50%, 60%, 70%, 80%, 90%, or 95% of the binding of the reference antibody to its antigen. Conversely, the reference antibody inhibits more than 50%, 60%, 70%, 80%, 90%, or 95% of the binding of the antibody to its antigen. The binding of an antibody to its antigen can be measured by affinity (e.g., equilibrium dissociation constant).

Methods for determining affinity are known in the art.

An antibody that shows the same or similar binding affinity and/or specificity as a reference antibody refers to an antibody that is capable of having at least more than 50%, 60%, 70%, 80%, 90%, or 95% of the binding affinity and/or specificity of the reference antibody. This can be determined by any method known in the art for determining binding affinity and/or specificity. "Complementarity determining region" or "CDR region" or "CDR" is a region in an antibody variable domain that is highly variable in sequence and forms a structurally defined loop ("hypervariable loop") and/or comprises antigen-contacting residues ("antigen contact site"). CDRs are primarily responsible for binding to antigen epitopes. The CDRs of heavy and light chains are generally referred to as CDR1, CDR2, and CDR3, which are numbered sequentially from N-terminus. The CDRs located in a heavy chain variable domain of an antibody are referred to as HCDR1, HCDR2, and HCDR3, whereas the CDRs located in a light chain variable domain of an antibody are referred to as LCDR1, LCDR2, and LCDR3. In a given amino acid sequence of a light chain variable region or a heavy chain variable region, the exact amino acid sequence boundary of each CDR can be determined using any one or a combination of many well-known antibody CDR assignment systems including, e.g., Chothia based on the three-dimensional structure of antibodies and the topology of the CDR loops (Chothia et al. (1989) *Nature* 342:877-883; Al-Lazikani et al., *Standard conformations for the canonical structures of immunoglobulins, Journal of Molecular Biology*, 273:927-948 (1997)), Kabat based on antibody sequence variability (Kabat et al., *Sequences of Proteins of Immunological Interest*, 4th edition, U.S. Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on the affinity propagation clustering using a large number of crystal structures.

For example, according to different CDR determination schemes, the residues of each CDR are as follows.

| CDR | Kabat scheme | AbM scheme | Chothia scheme | Contact scheme |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |
| | (Kabat numbering system) | | | |
| HCDR1 | H31-H35 | H26-H35 | H26-H32 | H30-H35 |
| | (Chothia numbering system) | | | |
| HCDR2 | H50-H65 | H50-H58 | H53-H55 | H47-H58 |
| HCDR3 | H95-H102 | H95-H102 | H96-H101 | H93-H101 |
| | (Kabat numbering system) | | | |

CDRs can also be determined based on having the same Kabat numbering positions as a reference CDR sequence (e.g., any of the exemplary CDRs of the present invention).

Unless otherwise stated, the term "CDR" or "CDR sequence" used herein encompasses CDR sequences determined by any of the schemes above.

Unless otherwise stated, residue positions of an antibody variable region (including heavy chain variable region residues and light chain variable region residues) are numbered according to the Kabat numbering system (Kabat et al., *Sequences of Proteins of Immunological Interest*, 5th Ed. Public Health Service, National Institutes of Health, Bethesda, Md. (1991)) herein.

In one embodiment, the boundaries of the CDRs of the antibodies disclosed herein are determined as per the AbM scheme, e.g., as shown by the sequences in Table 1.

It should be noted that boundaries of CDRs in variable regions of an antibody determined by different assignment systems may differ. That is, CDR sequences of variable regions of an antibody defined by different assignment systems differ. Therefore, when it comes to defining an antibody with specific CDR sequences defined in the present invention, the scope of antibody also encompasses such antibodies whose variable region sequences comprise the specific CDR sequences, but having claimed CDR boundaries different from the specific CDR boundaries defined by the present invention due to a different protocol (e.g., different assignment system rules or their combinations) applied.

Antibodies with different specificities (i.e., different binding sites for different antigens) have different CDRs (under the same assignment system). However, although CDRs differ from antibody to antibody, only a limited number of amino acid positions within the CDRs are directly involved in antigen binding. The smallest overlapping region can be determined using at least two of the Kabat, Chothia, AbM, Contact, and North methods, thereby providing a "minimal binding unit" for antigen binding. The minimal binding unit may be a sub-portion of the CDR. As will be clear to those skilled in the art, residues of the rest CDR sequences can be determined via antibody structure and protein folding. Therefore, any variants of the CDRs given herein are also considered in the present invention. For example, in a CDR variant, the amino acid residues in the minimal binding unit may remain unchanged, while the other CDR residues defined by Kabat or Chothia may be substituted by conservative amino acid residues.

As used herein, the term "IL-23 associated condition" or "IL-23 associated disease" refers to a condition that is induced by IL-23 activity and where IL-23 is usually abnormally expressed. The IL-23 associated condition includes immune system diseases, e.g., autoimmune diseases and inflammatory conditions. The disease includes (but is not limited to) rheumatoid arthritis (RA), systemic lupus erythematosus (SLE), scleroderma, Sjogren's syndrome, multiple sclerosis, psoriasis, psoriatic arthritis, inflammatory bowel diseases (e.g., ulcerative colitis and Crohn's disease), inflammation, asthma, idiopathic thrombocytopenic purpura (ITP), and ankylosing spondylitis.

As used herein, the term "immune system disease" includes diseases related to immune system disorders. The term "autoimmune disease" refers to a disease caused by the body's immune response to self-antigens resulting in damage to its own tissues. The term "inflammatory condition" used herein refers to such condition in which the pathology completely or partially attributes to, for example, changes in number, migration, or viability of immune system cells. The immune system cells include, for example, T cells, B cells, monocytes or macrophages, antigen presenting cells (APC), dendritic cells, microglia, NK cells, NKT cells, neutrophils, eosinophils, mastocytes, or any other cells specifically related to immunology, such as cytokine-producing endothelial cells or epithelial cells.

The term "therapeutic agent" used herein encompasses any substance effective in preventing or treating IL-23 associated diseases, including chemotherapeutic agents, cytokines, cytotoxic agents, other antibodies, small molecule drugs or immunomodulatory agents (such as anti-inflammatory agents or immunosuppressive agents).

The term "cytotoxic agent" used herein refers to a substance that inhibits or prevents cell functions and/or causes cell death or cell destruction.

"Chemotherapeutic agent" includes chemical compounds useful in the treatment of immune system diseases, including but not limited to alkylating agents, antimetabolites, natural products, antibiotics, enzymes, miscellaneous agents, hormones and antagonists, antiestrogens, antiandrogens, and non-steroidal antiandrogens, etc.

The term "small molecule drug" refers to a low molecular weight organic compound capable of regulating biological processes. "Small molecule" is defined as a molecule with a molecular weight of less than 10 kD, usually less than 2 kD and preferably less than 1 kD. The small molecule includes but is not limited to inorganic molecules, organic molecules, organic molecules containing inorganic components, molecules containing radioactive atoms, synthetic molecules, peptide mimetics, and antibody mimetics. As therapeutic agents, small molecules penetrate cells better, is less susceptible to degradation and is less likely to induce an immune response compared with large molecules. For descriptions of small molecules, such as peptide mimetics of antibodies and cytokines, and small molecule toxins, see, for example, Casset et al. (2003), *Biochem. Biophys. Res. Commun.*, 307:198-205; Muyldermans (2001), *J. Biotechnol.*, 74:277-302; Li (2000), *Nat. Biotechnol.*, 18:1251-1256; Apostolopoulos et al. (2002), *Curr. Med. Chem.*, 9:411-420; Monfardini et al. (2002), *Curr. Pharm. Des.*, 8:2185-2199; Domingues et al. (1999), *Nat. Struct. Biol.*, 6:652-656; Sato and Sone (2003), *Biochem. J.*, 371:603-608; U.S. Pat. No. 6,326,482.

The term "immunomodulatory agent" used herein refers to a natural or synthetic active agent or drug that suppresses or modulates an immune response. The immune response may be a humoral response or a cellular response. The immunomodulatory agent includes an immunosuppressive agent or an anti-inflammatory agent.

"Immunosuppressive agent", "immunosuppressive drug" or "immunosuppressant" used herein refers to a therapeutic agent used in immunosuppressive therapy to suppress or prevent the activity of the immune system. They are used clinically to prevent rejection of transplanted organs and tissues (such as bone marrow, heart, kidney, liver), and/or to treat autoimmune diseases or diseases most likely of autoimmune origin (such as rheumatoid arthritis, myasthenia gravis, systemic lupus erythematosus, ulcerative colitis, multiple sclerosis). Immunosuppressive drugs can be classified into 4 groups: glucocorticoid cytostatics; antibodies (including biological response modulators or DMARDs); drugs acting on immunophilins; and other drugs, including known chemotherapeutic agents used in the treatment of proliferative conditions. In particular, for multiple sclerosis, the antibody disclosed herein can be administered in combination with a novel myelin binding protein-like therapeutic agent called copaxone.

"Anti-inflammatory agent" or "anti-inflammatory drug" refers to a steroid or non-steroid therapeutic agent. Steroids, also known as corticosteroids, are drugs similar to cortisol, which is a hormone produced naturally by the adrenal glands. Steroids are mainly used to treat certain inflammatory conditions, e.g., systemic vasculitis (vascular inflammation) and myositis (muscle inflammation). Steroids can also be used to selectively treat inflammatory conditions such as: rheumatoid arthritis (a chronic inflammatory arthritis that occurs in lateral joints), systemic lupus erythematosus (a systemic disease caused by abnormal immune system function), and Sjogren's syndrome (a chronic condition that causes dry eyes and dry mouth).

Non-steroidal anti-inflammatory drugs, commonly abbreviated as NSAIDs, are drugs with analgesic, antipyretic and anti-inflammatory effects, and can alleviate pain, fever, and inflammation. The term "non-steroid" is used to distinguish such drugs from steroids, which (among a wide range of other effects) have similar eicosanoid inhibitory, anti-inflammatory effects. Generally, NSAIDs are used for symptom remission in the following conditions: rheumatoid arthritis; osteoarthritis; inflammatory arthropathy (e.g., ankylosing spondylitis, psoriatic arthritis, Reiter's syndrome); acute gout; dysmenorrhea; metastatic bone pain; headache and migraine; postoperative pain; mild to moderate pain attributed to inflammation and tissue damage; fever; and renal colic. NSAID includes salicylic acids, arylalkanoic acids, 2-arylpropionic acids, N-arylanthranilic acids (fenamic acids), oxicams, coxibs and N-sulphonanilides.

TNF (tumor necrosis factor) as described herein preferably includes pleiotropic homotrimeric cytokine TNFα, which is mainly secreted by monocytes and macrophages, and is also known to be produced by peripheral CD4$^+$ and CD8$^+$ T lymphocytes. TNFα is expressed in soluble form and in transmembrane form (the membrane-bound precursor form can be proteolytically cleaved into soluble homotrimers by a metalloproteinase TNFα converting enzyme (TACE)). It is believed that TNFα plays a role in the regulation of immune cells and is important in systemic inflammation, especially in the acute phase. Excessive TNFα is associated with various autoimmune diseases including RA, CD and psoriasis.

As used herein, "IL-17" such as IL-17A and IL-17F is a cytokine involved in inflammation. IL-17A induces production of inflammatory cytokines such as IL-10, TNF-α, IL-6 and IL-23 in synovial fibroblasts, monocytes and macrophages, all promoting inflammation and Th17 cell production. IL-17A also induces a large number of chemokines (including CXCL-1, CXCL-2, CXCL-5, CXCL-8, CCL-2 and CCL-20), leading to the recruitment of T cells, B cells, monocytes and neutrophils. Lundy, S. K., *Arthritis Res. Ther.*, 9:202(2007). IL-17F and IL-17A share the greatest homology (55%) and are also pro-inflammatory cytokines. Both IL-17A and IL-17F are produced by Th17 cells, while other IL-17 family members IL-17B, IL-17C, and IL-17D are produced by non-T cell sources. IL-17A and IL-17F are present in forms of IL-17A homodimer and IL-17F homodimer, or IL-17A/F heterodimer. Liang, S. C., et al., *J. Immunol.*, 179:7791-7799(2007). IL-17A is increased in serum and synovial fluid in rheumatoid arthritis, and is present in T cell-enriched region in synovium. Shahrara, S., *Arthritis Res. Ther.*, 10:R93(2005). IL-17A can also induce bone and cartilage damage. Effective blocking of IL-17 requires neutralization of IL-17A homodimer, IL-17F homodimer and IL-17A/F heterodimer.

"Functional Fc region" possesses the "effector functions" of Fc regions of native sequences. Exemplary "effector functions" include C1q binding, CDC, Fc receptor binding, ADCC, phagocytosis, cell surface receptor (e.g., B cell receptor, or BCR) down-regulation, and the like. Such effector functions generally require that the Fc region is associated with a binding domain (e.g., an antibody variable domain) and can be assessed using a variety of assays, such as those disclosed herein.

The term "Fc region" is used herein to define a C-terminus region of an immunoglobulin heavy chain, which comprises at least one portion of a constant region. The term includes Fc regions of native sequences and variant Fc regions. In certain embodiments, a human IgG heavy chain Fc region extends from Cys226 or Pro230 to the carbonyl end of the heavy chain. However, the C-terminal lysine (Lys447) of the Fc region may or may not be present. Unless otherwise stated, the numbering of amino acid residues in the Fc region or constant region is based on an EU numbering system, which is also called EU index as described in Kabat et al., *Sequences of Proteins of Immunological Interest*, 5$^{th}$ Ed. Public Health Service, National Institutes of Health, Bethesda, M D, 1991.

"Antibody in IgG form" refers to the heavy chain constant region of the antibody belonging to the IgG form. Heavy chain constant regions of all antibodies of the same type are identical, and heavy chain constant regions of antibodies of different types are different. For example, an antibody in the form of IgG1 refers to the Ig domain of its heavy chain constant region being an Ig domain of an IgG1.

The term "effective amount" refers to an amount or dosage of the antibody, fragment, conjugate or composition disclosed herein which generates expected effects in a patient in need of treatment or prevention after administered to the patient in a single or multiple doses. The effective amount can be easily determined by an attending physician as a person skilled in the art by considering a variety of factors as follows: species such as mammals; its size, age, and general health condition; the specific disease involved; the extent or severity of the disease; response in an individual patient; specific antibody administered; route of administration; bioavailability characteristics of the administered preparation; selected dosage regimen; and use of any concomitant therapy.

The "therapeutically effective amount" refers to an amount effective to achieve a desired therapeutic result at a necessary dosage for a necessary period of time. The therapeutically effective amount of an antibody or antibody fragment, or conjugate or composition thereof may vary depending on a variety of factors such as disease state, age, sex, and weight of an individual, and the ability of the antibody or antibody portion to elicit a desired response in an individual. The therapeutically effective amount is also such an amount that any toxic or undesired effect of the antibody or antibody fragment, or conjugate or composition thereof is inferior to the therapeutically beneficial effect. "Therapeutically effective amount" preferably inhibits a measurable parameter (e.g., swelling rate, etc.) by at least about 20%, more preferably at least about 40%, even more preferably at least about 50%, 60%, or 70%, and still more preferably at least about 80% or 90%, relative to untreated subjects. The ability of a compound to inhibit a measurable parameter (e.g., swelling rate) can be evaluated in an animal model system that predicts efficacy in human autoimmune diseases or inflammation.

The "prophylactically effective amount" refers to an amount effective to achieve a desired prophylactic result at a necessary dosage for a necessary period of time. Generally, since a prophylactic dose is administered in a subject before or at an earlier stage of a disease, a prophylactically effective amount will be less than a therapeutically effective amount.

The terms "host cell", "host cell line" and "host cell culture" are used interchangeably and refer to cells into which exogenous nucleic acids are introduced, including progenies of such cells. Host cells include "transformants" and "transformed cells", which include primary transformed cells and progenies derived therefrom, regardless of the number of passages. A generation may not be completely identical in nucleic acid content to the parent cell, but may contain mutations. Mutant generations having the same function or bioactivity that are screened or selected from the initially transformed cells are included herein.

"Human antibody" refers to an antibody having an amino acid sequence which corresponds to the amino acid sequence of an antibody generated by a human or human cell or derived from a non-human source that utilizes human antibody libraries or other human antibody encoding sequences. This definition of a human antibody explicitly excludes humanized antibodies comprising non-human antigen-binding residues.

"Humanized" antibody refers to a chimeric antibody comprising amino acid residues from non-human CDRs and amino acid residues from human FRs. In some embodiments, a humanized antibody will comprise at least one, or generally two of substantially all variable domains in which all or substantially all CDRs (e.g., CDRs) correspond to those of a non-human antibody, and all or substantially all FRs correspond to those of a human antibody. A humanized antibody may optionally comprise at least a portion of an antibody constant region derived from a human antibody. The "humanized form" of an antibody (such as a non-human antibody) refers to an antibody that has been humanized.

"Immunoconjugate" is an antibody conjugated to one or more other substances, including but not limited to cytotoxic agents or labels.

The term "label" used herein refers to a compound or composition which is directly or indirectly conjugated or fused to an agent, such as a polynucleotide probe or an antibody, and facilitates the detection of the agent to which it is conjugated or fused. The label itself can be detectable (e.g., a radioisotope label or a fluorescent label) or can catalyze a chemical change to a detectable substrate compound or composition in the case of enzymatic labeling. The term is intended to encompass direct labeling of a probe or an antibody by coupling (i.e., physical linking) a detectable substance to the probe or an antibody and indirect labeling of a probe or antibody by reacting with another reagent which is directly labeled. Examples of indirect labeling include detection of a primary antibody using a fluorescently labeled secondary antibody, and end labeling of a biotinylated DNA probe such that it can be detected with a fluorescently labeled streptavidin.

"Individual" or "subject" includes mammals. The mammals include, but are not limited to, domestic animals (e.g., cattle, goats, cats, dogs, and horses), primates (e.g., human and non-human primates such as monkeys), rabbits, and rodents (e.g., mice and rats). In some embodiments, the individual or subject is a human.

An "isolated" antibody is an antibody which has been separated from components of its natural environment. In some embodiments, the antibody is purified to a purity greater than 95% or 99% as determined by, e.g., electrophoresis (e.g., SDS-PAGE, isoelectric focusing (IEF) and capillary electrophoresis) or chromatography (e.g., ion exchange or reverse-phase HPLC). For a review of methods for assessing antibody purity, see, for example, Flatman et al., *J. Chromatogr.*, B848:79-87 (2007).

"Isolated nucleic acid encoding an anti-IL-23p19 antibody or a fragment thereof" refers to one or more nucleic acid molecules encoding an antibody heavy or light chain (or fragment thereof), including such nucleic acid molecules in a single vector or separate vectors, and such nucleic acid molecules present at one or more positions in a host cell.

The calculation of sequence identity between sequences is performed as follows.

To determine the percent identity of two amino acid sequences or two nucleic acid sequences, the sequences are aligned for optimal comparison purposes (e.g., for optimal alignment, gaps can be introduced in one or both of the first and second amino acid sequences or nucleic acid sequences, or non-homologous sequences can be discarded for comparison). In one preferred embodiment, for comparison purposes, the length of the aligned reference sequence is at least 30%, preferably at least 40%, more preferably at least 50% or 60%, and even more preferably at least 70%, 80%, 90%, or 100% of the length of the reference sequence. Amino acid residues or nucleotides at corresponding amino acid positions or nucleotide positions are then compared. When a position in the first sequence is occupied by the same amino acid residue or nucleotide at the corresponding position in the second sequence, the molecules are identical at this position.

A mathematical algorithm can be used to compare the sequences and calculate percent identity between two sequences. In one preferred embodiment, the percent identity between two amino acid sequences is determined with the Needlema and Wunsch algorithm ((1970) J. Mol. Biol., 48:444-453) which has been integrated into the GAP program of the GCG software package, using the Blossom 62 matrix or PAM250 matrix and gap weights of 16, 14, 12, 10, 8, 6, or 4 and length weights of 1, 2, 3, 4, 5, or 6. In another preferred embodiment, the percent identity between two nucleotide acid sequences is determined with the GAP program of the GCG software package, using the NWSgap-dna.CMP matrix and gap weights of 40, 50, 60, 70, or 80 and length weights of 1, 2, 3, 4, 5, or 6. A particularly preferred parameter set (and one that should be used unless otherwise stated) is a Blossom 62 scoring matrix with a gap penalty of 12, a gap extension penalty of 4, and a frameshift gap penalty of 5.

The percent identity between two amino acid sequences or nucleotide sequences can also be determined with PAM120 weighted remainder table, gap length penalty of 12 and gap penalty of 4, using the E. Meyers and W. Miller algorithms which have been incorporated into the ALIGN program (version 2.0) ((1989) CABIOS, 4:11-17).

Additionally or alternatively, the nucleic acid sequences and protein sequences described herein can be further used as "query sequences" to perform searches against public databases to, e.g., identify other family member sequences or related sequences.

The term "pharmaceutical excipient" refers to diluents, adjuvants (e.g., Freund's adjuvants (complete and incomplete)), carriers or stabilizers, etc., which are administered with the active substance.

The term "pharmaceutical composition" refers to such a composition that exists in a form allowing effective biological activity of the active ingredient contained therein, and does not contain additional ingredients having unacceptable toxicity to a subject to which the composition is administered.

The term "combination product" refers to a kit with a fixed combination, a non-fixed combination, or a part for combined administration in the form of a dose unit, wherein two or more therapeutic agents can be independently administered simultaneously or separately administered at intervals of time, especially when these intervals allow combination partners to exhibit collaboration, such as synergistic effect. The term "fixed combination" means that the antibody disclosed herein and a combined partner (e.g., other therapeutic agents, such as immunomodulatory agents, such as immunosuppressive agents or anti-inflammatory agents) are administered to a patient simultaneously in the form of a single entity or dose. The term "non-fixed combination" means that the antibody disclosed herein and a combined partner (e.g., other therapeutic agents, such as immunomodulatory agents, such as immunosuppressive agents or anti-inflammatory agents) are administered to a patient as separate entities simultaneously, in parallel, or sequentially, without specific time limitation, wherein such administration provides therapeutically effective levels of the two compounds in the patient. The latter is also applicable to a cocktail therapy, e.g., administration of three or more therapeutic agents. In one preferred embodiment, the drug combination is a non-fixed combination.

The term "combination therapy" refers to the administration of two or more therapeutic agents or modalities (e.g., radiation therapy or surgery) to treat IL-23 associated diseases as described in this disclosure. Such administration includes co-administration of these therapeutic agents in a substantially simultaneous manner, for example, in a single capsule with a fixed proportion of active ingredients. Alternatively, such administration includes co-administration of each active ingredient in a variety of or separate containers (such as tablets, capsules, powder and liquid). The powder and/or liquid can be reconstituted or diluted to a desired dosage before administration. In addition, such administration also includes using each type of therapeutic agents in a sequential manner at approximately the same time or at different times. In any case, the therapeutic regimen will provide the beneficial effect of the drug combination in the treatment of disorders or symptoms described herein.

As used herein, "treatment" (or "treat" or "treating") refers to slowing, interrupting, arresting, alleviating, stopping, reducing, or reversing the progression or severity of an existing symptom, disorder, condition, or disease.

As used herein, "prevention" (or "prevent" or "preventing") includes the inhibition of the onset or progression of a disease or disorder or a symptom of a specific disease or disorder. In some embodiments, subjects with family history of immune system diseases (autoimmune diseases or inflammation) are candidates for preventive regimens. Generally, in the context of immune system diseases (autoimmune diseases or inflammation), the term "prevention" refers to the administration of a drug prior to the onset of conditions or symptoms of immune system diseases (autoimmune diseases or inflammation), particularly in subjects at risk of immune system diseases (autoimmune diseases or inflammation).

The term "vector" used herein refers to a nucleic acid molecule capable of proliferating another nucleic acid to which it is linked. The term includes vectors that serve as self-replicating nucleic acid structures as well as vectors binding to the genome of a host cell into which they have been introduced. Some vectors are capable of directing the expression of a nucleic acid to which they are operably linked. Such vectors are called "expression vectors" herein.

"Subject/patient sample" refers to a collection of cells or fluids obtained from a patient or a subject. The source of tissue or cell samples can be solid tissues, e.g., from fresh, frozen and/or preserved organ or tissue samples or biopsy samples or puncture samples; blood or any blood component; body fluids such as cerebrospinal fluids, amniotic fluids, peritoneal fluids, or interstitial fluids; and cells from a subject at any time during pregnancy or development. Tissue samples may comprise compounds which are naturally not mixed with tissues, such as preservatives, anticoagulants, buffers, fixatives, nutrients, antibiotics, and the like.

II. Antibody

In some embodiments, the anti-IL-23p19 antibody or the fragment thereof disclosed herein binds to IL-23p19 (e.g., human IL-23p19 in human IL-23 or cynomolgus monkey IL-23p19 in cynomolgus monkey IL-23) with high affinity, for example, binding to IL-23p19 with an equilibrium dissociation constant ($K_D$) less than about 10 nM, preferably, less than or equal to about 5 nM, 4 nM, or 3 nM, and most preferably, less than or equal to about 2 nM, 1.9 nM, 1.8 nM, 1.79 nM, 1.78 nM, 1.77 nM, 1.76 nM, 1.75 nM, 1.74 nM, 1.73 nM, 1.72 nM, 1.71 nM, 1.7 nM, 1.69 nM, 1.68 nM, 1.67 nM, 1.66 nM, 1.65 nM, 1.64 nM, 1.63 nM, 1.62 nM, 1.61 nM, 1.6 nM, 1.55 nM, 1.5 nM, 1.45 nM, 1.4 nM, 1.35 nM, 1.3 nM, 1.25 nM, 1.2 nM, 1.15 nM, 1.1 nM, 1.05 nM, 1 nM, 0.95 nM, 0.9 nM, 0.85 nM, 0.8 nM, 0.75 nM, 0.7 nM, 0.69 nM, 0.68 nM, 0.67 nM, 0.66 nM, 0.65 nM, 0.64 nM, 0.63 nM, 0.62 nM, 0.61 nM, 0.6 nM, 0.59 nM, 0.58 nM, 0.57 nM, 0.56 nM, 0.55 nM, 0.54 nM, 0.53 nM, 0.52 nM, 0.51 nM, 0.5 nM, 0.49 nM, 0.48 nM, 0.47 nM, 0.46 nM, 0.45 nM, 0.44 nM, 0.43 nM, 0.42 nM, 0.41 nM, 0.4 nM, 0.39 nM, 0.38 nM, or 0.37 nM. In some embodiments, the anti-IL-23p19 antibody disclosed herein binds to IL-23p19 with a $K_D$ of 0.1 nM-3 nM, preferably 0.2 nM-2 nM, 0.2 nM-1.9 nM, 0.2 nM-1.8 nM, 0.3 nM-2 nM, 0.3 nM-1.9 nM, 0.3 nM-1.8 nM, 0.4 nM-2 nM, 0.4 nM-1.9 nM, 0.4 nM-1.8 nM, 0.5 nM-2 nM, 0.5 nM-1.9 nM, 0.5 nM-1.8 nM, 0.6 nM-2 nM, 0.6 nM-1.9 nM, 0.6 nM-1.8 nM. In some embodiments, the IL-23p19 is human IL-23p19. In some embodiments, the IL-23p19 is cynomolgus monkey IL-23p19. In some embodiments, the antibody binding affinity is determined using biological optical interferometry (e.g., Fortebio affinity assay).

In some embodiments, the antibody or the fragment thereof disclosed herein inhibits the secretion of IL-17 in cells (e.g., spleen cells) through binding to IL-23p19 molecule, for example, the inhibition rate of the antibody or the fragment thereof disclosed herein on IL-17 secretion in cells is up to 50%, 60%, 70%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, the antibody or the fragment thereof disclosed herein (optionally combined with treatment modalities and/or other therapeutic agents, such as immunomodulatory agents) can prevent or treat IL-23 associated diseases, e.g., immune system diseases (such as autoimmune diseases or inflammation). In some embodiments, the autoimmune disease is, for example, psoriasis, Crohn's disease, rheumatoid arthritis, ankylosing spondylitis, or psoriatic arthritis, etc.

In some embodiments, the anti-IL-23p19 antibody or the antigen-binding fragment thereof disclosed herein comprises a heavy chain variable region (VH), wherein the VH comprises (i) three complementarity determining regions (CDRs) in a VH set forth in SEQ ID NO: 9 or 10, or (ii) relative to the sequence of (i), a sequence comprising a total of at least one and no more than 5, 4, 3, 2, or 1 amino acid alteration (preferably amino acid replacement, and more preferably conservative replacement) in the three CDRs.

In some embodiments, the anti-IL-23p19 antibody or the antigen-binding fragment thereof disclosed herein comprises a light chain variable region (VL), wherein the VL comprises: (i) three complementarity determining regions (CDRs) in a VL set forth in SEQ ID NO: 11 or 12; or (ii) relative to the sequence of (i), a sequence comprising a total of at least one and no more than 5, 4, 3, 2, or 1 amino acid alteration (preferably amino acid replacement, and more preferably conservative replacement) in the three CDRs.

In some embodiments, the anti-IL-23p19 antibody or the antigen-binding fragment thereof disclosed herein comprises a heavy chain variable region VH and a light chain variable region VL, wherein
(a) the VH comprises:
(i) three complementarity determining regions (CDRs) in a VH set forth in SEQ ID NO: 9 or 10, or
(ii) relative to the sequence of (i), a sequence comprising a total of at least one and no more than 5, 4, 3, 2, or 1 amino acid alteration (preferably amino acid replacement, and more preferably conservative replacement) in the three CDRs; and/or
(b) the VL comprises:
(i) three complementarity determining regions (CDRs) in a VL set forth in SEQ ID NO: 11 or 12; or
(ii) relative to the sequence of (i), a sequence comprising a total of at least one and no more than 5, 4, 3, 2, or 1 amino acid alteration (preferably amino acid replacement, and more preferably conservative replacement) in the three CDRs.

In a preferred embodiment, the VH comprises or consists of an amino acid sequence selected from SEQ ID NOs: 9 and 10.

In a preferred embodiment, the VL comprises or consists of an amino acid sequence selected from SEQ ID NOs: 11 and 12.

In a preferred embodiment, the anti-IL-23p19 antibody or the antigen-binding fragment thereof disclosed herein comprises
(i) three complementarity determining regions in the heavy chain variable region (HCDR) set forth in SEQ ID NO: 9 or 10, and three complementarity determining regions in the light chain variable region (LCDR) set forth in SEQ ID NO: 11 or 12.

In some embodiments, the anti-IL-23p19 antibody or the antigen-binding fragment thereof disclosed herein comprises a heavy chain variable region (VH) and/or a light chain variable region (VL), wherein
(i) the VH comprises complementary determining regions (CDRs) of HCDR1, HCDR2 and HCDR3, wherein the HCDR1 comprises or consists of an amino acid sequence of SEQ ID NO: 1, or the HCDR1 comprises an amino acid sequence having one, two, or three alterations (preferably amino acid replacements, preferably conservative replacements) compared with an amino acid sequence of SEQ ID NO: 1; the HCDR2 comprises or consists of an amino acid sequence selected from SEQ ID NOs: 2, 3, and 23, or the HCDR2 comprises an amino acid sequence having one, two, or three alterations (preferably amino acid replacements, preferably conservative replacements) compared with an amino acid sequence selected from SEQ ID NO: 2, 3, and 23; the HCDR3 comprises or consists of an amino acid sequence of SEQ ID NO: 4, or the HCDR3 comprises an amino acid sequence having one, two, or three alterations (preferably amino acid replacements, preferably conservative replacements) compared with an amino acid sequence of SEQ ID NO: 4; and/or
(ii) the VL comprises complementary determining regions (CDRs) of LCDR1, LCDR2 and LCDR3, wherein the LCDR1 comprises or consists of an amino acid sequence of SEQ ID NO: 5, or the LCDR1 comprises an amino acid sequence having one, two, or three alterations (preferably amino acid replacements, preferably conservative replacements) compared with an amino acid sequence of SEQ ID NO: 5; the LCDR2 comprises or consists of an amino acid sequence of SEQ ID NO: 6, or the LCDR2 comprises an amino acid sequence having one, two, or three alterations (preferably amino acid replacements, preferably conservative replacements) compared with an amino acid sequence of SEQ ID NO: 6; the LCDR3 comprises or consists of an amino acid sequence selected from SEQ ID NOs: 7, 8, and 24, or the LCDR3 comprises an amino acid sequence having one, two, or three alterations (preferably amino acid replacements, preferably conservative replacements) compared with an amino acid sequence selected from SEQ ID NOs: 7, 8, and 24.

In a preferred embodiment, an anti-IL-23p19 antibody or an antigen-binding fragment thereof comprising a heavy chain variable region (VH) and a light chain variable region (VL) is provided, wherein
(a) the VH comprises:
(i) a combination of HCDR1, HCDR2, and HCDR3 shown in Table A; or
(ii) a variant of the HCDR combination in (i), comprising a total of at least one and no more than 5, 4, 3, 2, or 1 amino acid alteration (preferably amino acid replacement, and more preferably conservative replacement) in the three CDRs;
and/or
(b) the VL comprises
(i) a combination of LCDR1, LCDR2, and LCDR3 shown in Table A; or
(ii) a variant of the LCDR combination of (i), comprising a total of at least one and no more than 5, 4, 3, 2, or 1 amino acid alteration (preferably amino acid replacement, and more preferably conservative replacement) in the three CDRs.

In a preferred embodiment, an anti-IL-23p19 antibody or an antigen-binding fragment thereof comprising a heavy chain variable region (VH) and a light chain variable region (VL) is provided, wherein the VH comprises complementarity determining regions (CDRs) of HCDR1, HCDR2 and HCDR3; the VL comprises complementarity determining regions (CDRs) of LCDR1, LCDR2 and LCDR3; and combinations of HCDR1, HCDR2, HCDR3, LCDR1, LCDR2, and LCDR3 of the antibody or the antigen-binding fragment thereof are shown in the following table (Table A):

TABLE A

Exemplary combinations of HCDR1, HCDR2, HCDR3, LCDR1, LCDR2, and LCDR3 of the antibody or the antigen-binding fragment thereof disclosed herein

| Combinations | HCDR1, which comprises or consists of an amino acid sequence set forth in the following SEQ ID Nos | HCDR2, which comprises or consists of an amino acid sequence set forth in the following SEQ ID Nos | HCDR3, which comprises or consists of an amino acid sequence set forth in the following SEQ ID Nos | LCDR1, which comprises or consists of an amino acid sequence set forth in the following SEQ ID Nos | LCDR2, which comprises or consists of an amino acid sequence set forth in the following SEQ ID Nos | LCDR3, which comprises or consists of an amino acid sequence set forth in the following SEQ ID Nos |
|---|---|---|---|---|---|---|
| (1) | SEQ ID NO: 1 | SEQ ID NO: 2 | SEQ ID NO: 4 | SEQ ID NO: 5 | SEQ ID NO: 6 | SEQ ID NO: 7 |
| (2) | SEQ ID NO: 1 | SEQ ID NO: 3 | SEQ ID NO: 4 | SEQ ID NO: 5 | SEQ ID NO: 6 | SEQ ID NO: 8 |
| (3) | SEQ ID NO: 1 | SEQ ID NO: 23 | SEQ ID NO: 4 | SEQ ID NO: 5 | SEQ ID NO: 6 | SEQ ID NO: 24 |

In some embodiments, the anti-IL-23p19 antibody or the antigen-binding fragment thereof disclosed herein comprises a heavy chain variable region VH and/or a light chain variable region VL, wherein (a) the heavy chain variable region VH (i) comprises or consists of an amino acid sequence having at least 90%, 91%, 92%, 93%, 94%, 95%, 96%, 97%, 98%, or 99% identity to an amino acid sequence selected from SEQ ID NOs: 9 and 10;

(ii) comprises or consists of an amino acid sequence selected from SEQ ID NOs: 9 and 10, or (iii) comprises an amino acid sequence having 1 or more (preferably not more than 10, more preferably not more than 5, 4, 3, 2, or 1) amino acid alterations (preferably amino acid replacements, more preferably conservative amino acid replacements) compared with an amino acid sequence selected from SEQ ID NOs: 9 and 10, wherein preferably, the amino acid alterations are not in the CDRs;

and/or (b) the light chain variable region VL (i) comprises or consists of an amino acid sequence having at least 90%, 91%, 92%, 93%, 94%, 95%, 96%, 97%, 98%, or 99% identity to an amino acid sequence selected from SEQ ID NOs: 11 and 12;

(ii) comprises or consists of an amino acid sequence selected from SEQ ID NOs: 11 and 12, or (iii) comprises an amino acid sequence having 1 or more (preferably not more than 10, more preferably not more than 5, 4, 3, 2, or 1) amino acid alterations (preferably amino acid replacements, more preferably conservative amino acid replacements) compared with an amino acid sequence selected from SEQ ID NOs: 11 and 12, wherein preferably, the amino acid alterations are not in the CDRs;

In a preferred embodiment, an anti-IL-23p19 antibody or an antigen-binding fragment thereof comprising a heavy chain variable region (VH) and a light chain variable region (VL) is provided, wherein combinations of the heavy chain variable region VH and light chain variable region VL of the antibody or the antigen-binding fragment thereof are shown in the following table (Table B).

TABLE B

Exemplary combinations of heavy chain variable region VH and light chain variable region VL of the antibody or the antigen-binding fragment thereof disclosed herein

| Combinations | VH, which comprises or consists of an amino acid sequence set forth in the following SEQ ID NOs | VL, which comprises or consists of an amino acid sequence set forth in the following SEQ ID NOs |
|---|---|---|
| (1) | SEQ ID NO: 9 | SEQ ID NO: 11 |
| (2) | SEQ ID NO: 10 | SEQ ID NO: 12 |

In some embodiments, the anti-IL-23p19 antibody or the antigen-binding fragment thereof disclosed herein comprises a heavy chain and/or a light chain, wherein (a) the heavy chain (i) comprises or consists of an amino acid sequence having at least 85%, 90%, 91%, 92%, 93%, 94%, 95%, 96%, 97%, 98%, or 99% identity with an amino acid sequence selected from SEQ ID NOs: 13, 14 and 15;

(ii) comprises or consists of an amino acid sequence selected from SEQ ID NOs: 13, 14, and 15; or (iii) comprises an amino acid sequence having 1 or more (preferably not more than 20 or 10, and more preferably not more than 5, 4, 3, 2, or 1) amino acid alterations (preferably amino acid replacements, and more preferably conservative amino acid replacements) compared with an amino acid sequence selected from SEQ ID NOs: 13, 14, and 15, wherein preferably, the amino acid alterations are not in the CDRs of the heavy chain, and more preferably, the amino acid alterations are not in the heavy chain variable region;
and/or
(b) the light chain
(i) comprises or consists of an amino acid sequence having at least 85%, 90%, 91%, 92%, 93%, 94%, 95%, 96%, 97%, 98%. or 99% identity with an amino acid sequence selected from SEQ ID NOs: 16 and 17;
(ii) comprises or consists of an amino acid sequence selected from SEQ ID NOs: 16 and 17, or
(iii) comprises an amino acid sequence having 1 or more (preferably not more than 20 or 10, and more preferably not more than 5, 4, 3, 2, or 1) amino acid alterations (preferably amino acid replacements, and more preferably conservative amino acid replacements) compared with an amino acid sequence selected from SEQ ID NOs: 16 and 17, wherein preferably, the amino acid alterations are not in the CDRs of the light chain, and more preferably, the amino acid alterations are not in the light chain variable region.

In a preferred embodiment, an anti-IL-23p19 antibody or an antigen-binding fragment thereof comprising a heavy chain and a light chain is provided, wherein combinations of the heavy and light chains of the antibody or the antigen-binding fragment thereof are shown in the following table (Table C).

TABLE C

Exemplary combinations of heavy chain and light chain of the antibody or the antigen-binding fragment thereof disclosed herein

| Combinations | Heavy chain, which comprises or consists of an amino acid sequence set forth in the following SEQ ID NOs | Light chain, which comprises or consists of an amino acid sequence set forth in the following SEQ ID NOs |
|---|---|---|
| (1) | SEQ ID NO: 13 | SEQ ID NO: 16 |
| (2) | SEQ ID NO: 14 | SEQ ID NO: 17 |
| (3) | SEQ ID NO: 15 | SEQ ID NO: 17 |

In some embodiments, the heavy chain and/or light chain of the anti-IL-23p19 antibody or the fragment thereof disclosed herein further comprises a signal peptide sequence, such as METDTLLLWVLLLWVPGSTG (SEQ ID NO: 25).

In one embodiment of the present invention, the amino acid alteration described herein includes amino acid replacement, insertion or deletion. Preferably, the amino acid alteration described herein is an amino acid replacement, preferably a conservative replacement.

In a preferred embodiment, the amino acid alteration described herein occurs in a region outside the CDR (e.g., in FR). More preferably, the amino acid alteration described herein occurs in a region outside the heavy chain variable region and/or outside the light chain variable region.

In some embodiments, the replacement is a conservative replacement. A conservative replacement refers to the replacement of an amino acid by another amino acid of the same class, e.g., the replacement of an acidic amino acid by another acidic amino acid, the replacement of a basic amino acid by another basic amino acid, or the replacement of a neutral amino acid by another neutral amino acid. Exemplary replacements are shown in Table D below.

TABLE D

| Primitive residue | Exemplary replacement | Preferred conservative amino acid replacement |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Nle | Leu |
| Leu (L) | Nle, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Nle | Leu |

In certain embodiments, the replacement occurs in the CDRs of the antibody. Generally, the obtained variant has modifications (e.g., improvements) in certain biological properties (e.g., increased affinity) relative to the parent antibody and/or will have certain biological properties substantially retained from the parent antibody. Exemplary replacement variants are affinity mature antibodies.

In certain embodiments, the antibody disclosed herein is altered to increase or decrease the extent to which the antibody is glycosylated. Addition or deletion of glycosylation sites to an antibody can be conveniently achieved by altering the amino acid sequence such that one or more glycosylation sites are created or removed. When the antibody comprises an Fc region, carbohydrate attached thereto can be altered. In some applications, modifications that remove undesired glycosylation sites can be useful, for example, removing fucose modules to enhance antibody-dependent cellular cytotoxicity (ADCC) (see Shield et al., (2002) JBC277:26733). In other applications, galactosidylation modification can be carried out to modify complement-dependent cytotoxicity (CDC).

In certain embodiments, one or more amino acid modifications can be introduced into the Fc region of the antibody disclosed herein, thereby producing an Fc region variant such that, for example, the affinity of the antibody or the efficacy of the antibody in treating diseases is enhanced. The Fc region variant may comprise a human Fc region sequence (such as human IgG1, IgG2, IgG3, or IgG4 Fc region) comprising an amino acid modification (such as replacement) at one or more amino acid positions. For examples of the Fc variant, see U.S. Pat. Nos. 7,332,581, 6,737,056, 6,737,056; WO 2004/056312 and Shields, et al., *J. Biol.*

Chem. 9(2):6591-6604(2001), U.S. Pat. No. 6,194,551, WO 99/51642 and Idusogie, et al., *J. Immunol.* 164:4178-4184 (2000), U.S. Pat. No. 7,371,826, Duncan & Winter, *Nature* 322:738-40(1988); U.S. Pat. Nos. 5,648,260; 5,624,821; and WO 94/29351.

In one embodiment of the present invention, substitution mutations (M252Y/S254T/T256E) are introduced in the Fc region of the antibody disclosed herein to enhance the ability of binding to human FcRn, in order to extend the half-life in vivo.

In certain embodiments, antibodies modified by cysteine engineering may need to be produced, such as "sulfo-MAb", wherein one or more residues of the antibodies are replaced by cysteine residues. A cysteine-modified antibody can be produced as described, for example, in U.S. Pat. No. 7,521, 541.

In certain embodiments, the antibody disclosed herein can be further modified to comprise other non-protein portions known in the art and readily available. Suitable portions for antibody derivatization include, but are not limited to, water-soluble polymers. Non-limiting examples of water-soluble polymers include, but are not limited to, polyethylene glycol (PEG), ethylene glycol/propylene glycol copolymer, carboxymethyl cellulose, glucan, polyvinyl alcohol, polyvinylpyrrolidone, poly-1,3-dioxane, poly-1,3,6-trioxane, ethylene/maleic anhydride copolymer, polyamino acid (homopolymer or random copolymer), and glucan or poly(n-vinylpyrrolidone), polyethylene glycol, propylene glycol homopolymer, polypropylene oxide/ethylene oxide copolymer, polyoxyethylated polyol (such as glycerol), polyvinyl alcohol, and mixtures thereof.

In some embodiments, the anti-IL-23p19 antibody or the antigen-binding fragment thereof disclosed herein has one or more of the following properties:
(i) showing identical or similar binding affinity and/or specificity for IL-23p19 compared to the antibody disclosed herein (e.g., any of the antibodies listed in Table 3);
(ii) inhibiting (e.g., competitively inhibiting) the binding of the antibody disclosed herein (e.g., any of the antibodies listed in Table 3) to IL-23p19;
(iii) binding to the same or overlapping epitope as the antibody disclosed herein (e.g., any of the antibodies listed in Table 3);
(iv) competing with the antibody disclosed herein (e.g., any of the antibodies listed in Table 3) for binding to IL-23p19; and
(v) having one or more biological properties of the antibody disclosed herein (e.g., any of the antibodies listed in Table 3).

In some embodiments, the anti-IL-23p19 antibody disclosed herein is an antibody in the form of IgG1, IgG2, or IgG4.

In some embodiments, the anti-IL-23p19 antibody is a monoclonal antibody.

In some embodiments, the anti-IL-23p19 antibody is humanized. Different methods for humanizing antibodies are known to those skilled, as summarized by Almagro & Fransson, the content of which is incorporated in its entirety herein by reference (Almagro J. C. and Fransson J (2008) *Frontiers in Bioscience* 13:1619-1633).

In some embodiments, the anti-IL-23p19 antibody is a human antibody. The human antibody can be prepared using a variety of techniques known in the art. The human antibody is generally described in van Dijk and van de Winkel, *Curr. Opin. Pharmacol* 5:368-74(2001) and Lonberg, *Curr. Opin. Immunol* 20:450-459(2008).

In some embodiments, the anti-IL-23p19 antibody is a chimeric antibody.

In some embodiments, at least a portion of the framework sequence of the anti-IL-23p19 antibody is a human consensus framework sequence. In one embodiment, the anti-IL-23p19 antibody disclosed herein also includes an antibody fragment thereof, and preferably an antibody fragment selected from: Fab, Fab', Fab'-SH, Fv, single-chain variable fragment (e.g., scFv) or (Fab')$_2$, single-domain antibody, diabody (dAb), and linear antibody.

In some embodiments, the anti-IL-23p19 antibody molecule is in the form of a bispecific or multispecific antibody molecule. In one embodiment, the bispecific antibody molecule has a first binding specificity for IL-23p19 and a second binding specificity for TNF (e.g., TNFα) or IL-17 (e.g., IL-17A or IL-17F). In one embodiment, the bispecific antibody molecule binds to IL-23p19 and TNF or IL-17. The multispecific antibody molecule may have any combination of binding specificities for above molecules.

II. Nucleic Acid of the Invention and Host Cell Comprising Same

In one aspect, a nucleic acid encoding any of the above anti-IL-23p19 antibodies or fragments thereof is provided. In one embodiment, a vector comprising the nucleic acid is provided. In one embodiment, the vector is an expression vector. In one embodiment, a host cell comprising the nucleic acid or the vector is provided. In one embodiment, the host cell is eukaryotic. In another embodiment, the host cell is selected from a yeast cell, a mammal cell (e.g., CHO cell or 293 cell), and other cells suitable for preparing an antibody or an antigen-binding fragment thereof. In another embodiment, the host cell is prokaryotic.

In one aspect, the present invention provides a nucleic acid encoding any of the anti-IL-23p19 antibodies or fragments thereof described herein. The nucleic acid can include a nucleic acid encoding an amino acid sequence of the light chain variable region and/or heavy chain variable region of the antibody, or a nucleic acid encoding an amino acid sequence of the light chain and/or heavy chain of the antibody. Exemplary nucleic acid sequence encoding the heavy chain of the antibody includes a nucleic acid sequence having at least 80%, 85%, 90%, 91%, 92%, 93%, 94%, 95%, 96%, 97%, 98%, or 99% identity to a nucleic acid sequences selected from SEQ ID NOs: 18, 19, and 20, or includes a nucleic acid sequence selected from SEQ ID NOs: 18, 19, and 20. Exemplary nucleic acid sequence encoding the light chain of the antibody includes a nucleic acid sequence having at least 80%, 85%, 90%, 91%, 92%, 93%, 94%, 95%, 96%, 97%, 98%, or 99% identity to a nucleic acid sequences selected from SEQ ID NOs: 21 and 22, or includes a nucleic acid sequence selected from SEQ ID NOs: 21 and 22.

In one embodiment, one or more vectors comprising the nucleic acid are provided. In one embodiment, the vector is an expression vector, such as a eukaryotic expression vector. The vector includes, but is not limited to, a virus, a plasmid, a cosmid, a lambda phage, or a yeast artificial chromosome (YAC). In one embodiment, the vector is pTT5 vector.

In one embodiment, a host cell comprising the vector is provided. The suitable host cell for cloning or expressing the vector encoding the antibody includes prokaryotic cells or eukaryotic cells described herein. For example, the antibody may be produced in bacteria, particularly when glycosylation and Fc effector functions are not required. Expression of an antibody fragment and a polypeptide in bacteria is described in, for example, U.S. Pat. Nos. 5,648,237, 5,789, 199 and 5,840,523, and also described in Charlton, *Methods in Molecular Biology*, Vol. 248 (B. K. C. Lo, ed., Humana Press, Totowa, N J, 2003), pg. 245-254, which describes expression of antibody fragments in *E. coli*. After expression, the antibody can be isolated from bacterial cell paste in soluble fraction and can be further purified.

In one embodiment, the host cell is eukaryotic. In another embodiment, the host cell is selected from a yeast cell, a mammalian cell, or other cells suitable for preparing an antibody or an antigen-binding fragment thereof. For example, eukaryotic microorganisms, such as filamentous fungi or yeast, are suitable cloning or expression hosts for the vector encoding the antibody. For example, fungus and yeast strains in which a glycosylation pathway has been "humanized" may produce antibodies having a partial or full human glycosylation pattern. See Gerngross, *Nat. Biotech.*, 22:1409-1414 (2004), and Li et al., *Nat. Biotech.*, 24:210-215 (2006). Host cells suitable for expressing a glycosylated antibody are also derived from multicellular organisms (invertebrates and vertebrates). Vertebrate cells may also be used as hosts. For example, a mammalian cell line engineered to be suitable for suspension growth may be used. Other examples of useful mammalian host cell lines are monkey kidney CV1 cell line (COS-7) transformed with SV40, human embryonic kidney cell lines (293HEK or 293F or 293 cells, as described in, e.g., Graham et al., *J. Gen Virol.*, 36:59 (1977)) and the like. Other useful mammalian host cell lines include Chinese hamster ovary (CHO) cells, including DHFR-CHO cells (Urlaub et al., *Proc. Natl. Acad. Sci. USA* 77: 216 (1980)), CHO-S cells and the like; and myeloma cell lines such as Y0, NS0, and Sp2/0. For reviews of certain mammalian host cell lines suitable for antibody production, see, for example, Yazaki and Wu, *Methods in Molecular Biology*, Vol. 248 (B. K. C. Lo, ed., Humana Press, Totowa, NJ), pg. 255-268 (2003).

In one embodiment, a method for preparing an anti-IL-23p19 antibody or a fragment thereof (preferably an antigen-binding fragment) is provided, wherein the method comprises culturing the host cell under a condition suitable for expression of a nucleic acid encoding the antibody or the fragment thereof (preferably the antigen-binding fragment), and optionally isolating the antibody or the fragment thereof (preferably the antigen-binding fragment). In a certain embodiment, the method further comprises isolating the anti-IL-23p19 antibody or the fragment thereof (preferably the antigen-binding fragment) from the host cell.

In one embodiment, a method for preparing an anti-IL-23p19 antibody is provided, wherein the method comprises culturing the host cell comprising a nucleic acid encoding the antibody under a condition suitable for antibody expression, as provided above, and optionally isolating the antibody from the host cells (or host cell culture). For recombinant production of the anti-IL-23p19 antibody, a nucleic acid encoding the antibody (e.g., the antibody described above) is isolated and inserted into one or more vectors for further cloning and/or expression in the host cells. Such a nucleic acid can be easily isolated and sequenced by using conventional procedures (e.g., by using oligonucleotide probes that are capable of specifically binding to genes encoding heavy and light chains of antibodies).

III. Characterization

The anti-IL-23p19 antibodies provided herein can be identified, screened, or characterized for physical/chemical properties and/or bioactivity through a variety of assays known in the art. In one aspect, the antigen-binding activity of the antibody disclosed herein is analyzed, for example, by known methods such as ELISA, Western blotting and the like. IL-23p19 binding can be determined by methods known in the art, and exemplary methods are described herein. In some embodiments, biological optical interferometry (e.g., Fortebio affinity assay) or MSD is used.

In another aspect, antibodies that compete for binding to IL-23p19 with any of the anti-IL-23p19 antibodies disclosed herein can be characterized by competitive binding assay. In certain embodiments, such competitive antibodies bind to the same or an overlapping epitope (e.g., a linear or conformational epitope) as any of the anti-IL-23p19 antibodies disclosed herein. A detailed exemplary method for locating an epitope to which the antibody binds is described in Morris (1996) "Epitope Mapping Protocols", *Methods in Molecular Biology*, vol. 66 (Humana Press, Totowa, NJ). The present invention also provides an assay for identifying anti-IL-23p19 antibodies having biological activities. Biological activities can include, for example, binding to IL-23p19 (e.g., binding to human and/or cynomolgus monkey IL-23p19), inhibiting the induction of IL-17 secretion by IL-23, blocking IL-23 signaling pathway, and the like. Further provided is an antibody having such biological activities in vivo and/or in vitro.

In some embodiments, the antibody disclosed herein is characterized for such biological activities. Cells for use in any of the in vitro assays described above include cells that naturally express IL-23p19 or are engineered to express IL-23p19. Such cells also include cells that express IL-23p19 and cells that do not normally express IL-23p19 and have been transfected with DNA encoding IL-23p19.

It will be appreciated that any of the above assays can be performed on the immunoconjugate disclosed herein in place of or in addition to the anti-IL-23p19 antibody.

It will also be appreciated that any of the above assays can be performed on the anti-IL-23p19 antibody and other active agents.

IV. Immunoconjugates

In some embodiments, the present invention provides an immunoconjugate comprising any of the anti-IL-23p19 antibodies provided herein and additional substances, such as therapeutic agents, including chemotherapeutic agents, cytokines, cytotoxic agents, other antibodies, small-molecule drugs or immunomodulatory agents (e.g., anti-inflammatory agents or immunosuppressant agents). In one embodiment, the additional substances such as cytotoxic agents include any agents that are harmful to cells. Examples of the cytotoxic agent suitable for forming the immunoconjugate are known in the art. For example, the cytotoxic agent includes, but is not limited to: radioisotopes; growth inhibitors; enzymes and fragments thereof such as nucleases; antibiotics; toxins such as small-molecule toxins or enzymatically active toxins of bacterial, fungal, plant or animal sources, including fragments and/or variants thereof. See also U.S. 61/642,032 for other examples of forming immunoconjugates with the antibodies disclosed herein.

In some embodiments, the immunoconjugate is used to prevent or treat IL-23 associated diseases, e.g., immune system diseases (such as autoimmune diseases or inflammation). In some embodiments, the autoimmune disease is, for example, psoriasis, Crohn's disease, rheumatoid arthritis, ankylosing spondylitis, or psoriatic arthritis, etc.

V. Pharmaceutical Composition and Pharmaceutical Preparation

In some embodiments, the present invention provides a composition comprising any of the anti-IL-23p19 antibodies described herein or a fragment thereof (preferably an antigen-binding fragment thereof), or an immunoconjugate thereof, wherein, preferably, the composition is a pharmaceutical composition. In one embodiment, the composition further comprises pharmaceutical excipients. In one embodiment, the composition, e.g., the pharmaceutical composition, comprises the anti-IL-23p19 antibody or the fragment thereof, or the immunoconjugate thereof disclosed herein, and a combination of one or more additional therapeutic agents.

In some embodiments, the composition is used to prevent or treat IL-23 associated diseases, e.g., immune system diseases (such as autoimmune diseases or inflammation). In some embodiments, the autoimmune diseases are, for example, psoriasis, Crohn's disease, rheumatoid arthritis, ankylosing spondylitis, psoriatic arthritis and the like.

The present invention also includes a composition (including a pharmaceutical composition or a pharmaceutical preparation) comprising an anti-IL-23p19 antibody or an immunoconjugate thereof, or a composition (including a pharmaceutical composition or a pharmaceutical preparation) comprising a polynucleotide encoding the anti-IL-23p19 antibody. In certain embodiments, the composition comprises one or more antibodies binding to IL-23p19 or fragments thereof, or one or more polynucleotides encoding the one or more anti-IL-23p19 antibodies or fragments thereof. Such compositions can further comprise suitable pharmaceutical excipients, such as a pharmaceutical carrier known in the art, including buffers.

The pharmaceutical carrier applicable to the present invention may be sterile liquid, such as water and oil, including those derived from petroleum, animals, plants or synthesis, such as peanut oil, soybean oil, mineral oil, sesame oil, etc. Water is a preferred carrier when the pharmaceutical composition is administered intravenously. Saline solutions, aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, etc. For use and application of excipients, see *Handbook of Pharmaceutical Excipients*, the fifth edition, R. C. Rowe, P. J. Seskey and S. C. Owen, Pharmaceutical Press, London, Chicago. The composition may further comprise a small quantity of wetting agent, emulsifier, or pH buffer, if desired. The compositions may take the form of a solution, a suspension, an emulsion, a tablet, a pill, a capsule, a powder, a sustained release preparation, and the like. Oral preparations may comprise standard carriers, such as pharmaceutical grade mannitol, lactose, starch, magnesium stearate, and saccharin.

The pharmaceutical preparation, preferably in the form of a lyophilized preparation or an aqueous solution, comprising the anti-IL-23p19 antibody described herein can be prepared by mixing the anti-IL-23p19 antibody disclosed herein of desired purity with one or more optional pharmaceutical excipients (*Remington's Pharmaceutical Sciences*, 16th edition, Osol, A. ed. (1980)).

An exemplary lyophilized antibody preparation is described in U.S. Pat. No. 6,267,958. The aqueous antibody preparation includes those described in U.S. Pat. No. 6,171,586 and WO 2006/044908, and the latter preparation comprises a histidine-acetate buffer.

The pharmaceutical composition or preparation disclosed herein can further comprise one or more other active ingredients which are required for a specific indication being treated, preferably active ingredients having complementary activities that do not adversely affect one another. The active ingredients are suitably combined in an amount effective for an intended purpose. Exemplary active ingredients include chemotherapeutic agents, cytokines, cytotoxic agents, other antibodies, small-molecule drugs, immunomodulatory agents and the like.

A sustained release preparation can be formulated. Suitable examples of the sustained release preparation include a semipermeable matrix of a solid hydrophobic polymer containing an antibody.

The matrix is in the form of a shaped article, such as a film or a microcapsule.

For other components of the pharmaceutical preparation/pharmaceutical composition comprising the antibodies of the present invention, see also those disclosed in WO2008103473A1, WO2007076524A2 or WO2008103432A1, etc.

VI. Combination Products

In some embodiments, the present invention also provides a combination product comprising the antibody or the antigen-binding fragment thereof disclosed herein, or the immunoconjugate thereof, and one or more additional therapeutic agents (e.g., chemotherapeutic agents, cytokines, cytotoxic agents, other antibodies, small molecule drugs or immunomodulatory agents and the like). In some embodiments, the immunomodulatory agent is, for example, an immunosuppressant or an anti-inflammatory drug. In some embodiments, other antibody is, for example, an anti-TNF antibody or an anti-IL-17 antibody.

For suitable additional therapeutic agents that can be used in combination products with the antibodies of the present invention, see also those disclosed in WO2008103473A1, WO2007076524A2 or WO2008103432A1.

In some embodiments, the combination product is used for preventing or treating IL-23 associated diseases, e.g., immune system diseases (such as autoimmune diseases or inflammation). In some embodiments, the autoimmune disease is, for example, psoriasis, Crohn's disease, rheumatoid arthritis, ankylosing spondylitis, or psoriatic arthritis, etc.

VII. Use

In one aspect, the present invention provides a method for treating IL-23 associated diseases in a subject, comprising administering to a subject an effective amount of the anti-IL-23p19 antibody or the antigen-binding fragment, the immunoconjugate, the drug composition or the combination product thereof disclosed herein.

The subject can be a mammal, e.g., a primate, preferably a higher primate, e.g., a human (e.g., a patient having or at risk of having the disease described herein). In one embodiment, the subject has or is at risk of having the disease described herein (e.g., IL-23 associated diseases described herein, e.g., immune system diseases (such as autoimmune diseases or inflammation)). In certain embodiments, the subject is receiving or has received other therapies, e.g., anti-inflammatory drugs or immunosuppressive therapy and/or radiation therapy.

In some embodiments, the IL-23 associated diseases described herein include immune system diseases, e.g., autoimmune diseases or inflammation. The disease includes (but is not limited to) psoriasis, Crohn's disease, rheumatoid arthritis, ankylosing spondylitis, psoriatic arthritis and the like.

In one embodiment, the immune system disease is a disease that expresses an elevated level of IL-23p19.

In other aspects, the present invention provides use of the anti-IL-23p19 antibody or the fragment thereof disclosed herein in producing or preparing of a medicament for treating the associated diseases or conditions described herein.

In some embodiments, the antibody or the antibody fragment, the immunoconjugate, the composition, or the product disclosed herein delays onset of the conditions and/or symptoms associated with the conditions.

In some embodiments, the method for preventing or treating disclosed herein further comprises administering to the subject or individual the antibody molecule, the pharmaceutical composition or the immunoconjugate disclosed herein in combination with one or more additional therapies, e.g., therapeutic modalities and/or other therapeutic agents.

In some embodiments, the therapeutic modality includes surgery, radiation therapy (e.g., an external beam therapy that involves a three-dimensional conformal radiation therapy in which an irradiation region is designed), partial irradiation (e.g., an irradiation directed to a preselected target or an organ), focused irradiation, and the like.

In some embodiments, the therapeutic agent is selected from chemotherapeutic agents, cytokines, cytotoxic agents, other antibodies, small-molecule drugs, and immunomodulatory agents.

Other exemplary antibodies include, but are not limited to, anti-TNF antibodies or anti-IL-17 antibodies, e.g., anti-TNFα antibodies or anti-IL-17A antibodies or anti-IL-17F antibodies.

Exemplary immunomodulatory agents include immunosuppressants or anti-inflammatory agents. In some embodiments, the antibody combinations described herein can be administered separately (e.g., as separate antibodies) or in linkage (e.g., as a bispecific or trispecific antibody molecule). For more therapies or therapeutic agents that can be combined with anti-IL-23p19 antibodies or fragments thereof, see WO2008103473A1, WO2007076524A2 or WO2008103432A1.

Such combination therapies encompass both co-administration (e.g., two or more therapeutic agents are contained in the same preparation or separate preparations), and separate administrations, in which the antibody of the present invention can be administered prior to, concurrently with, and/or after the administration of other therapeutic agents and/or pharmaceuticals. In one embodiment, administration of the anti-IL-23p19 antibody and administration of the additional therapy are within about one month, within about one, two or three weeks, or within about 1, 2, 3, 4, 5, or 6 days from each other.

The therapeutically effective amount of the pharmaceutical composition comprising the anti-IL-23p19 antibody to be used will depend, for example, on the therapeutic background and objective. Those skilled in the art will understand that the appropriate dosage level for treatment will vary based partially on the following factors: the molecule delivered, the indication for use, the route of administration, and the patient's weight, body surface area or organ size and/or condition (age and general health status). In some embodiments, a clinician can titrate the dosage and change the route of administration to achieve best overall response.

The dosing frequency will depend on the pharmacokinetics of the specific anti-IL-23p19 antibody used in the preparation. Generally, the composition is administered until a dosage achieving desired efficacy. The antibody of the present invention can thus be administered in a single dose, or in two or more doses (which can containing the same or different amounts of the desired molecule) over a certain period of time, or by continuous infusion through an implanted device or catheter. The appropriate dosage can be determined by using appropriate dose-response data. In certain embodiments, the antibody can be administered to a patient for an extended period of time. In certain embodiments, the antibody is administered weekly, biweekly, monthly, bimonthly, every three months, every four months, every five months, or every six months.

The route of administration of the pharmaceutical composition is based on a known method, for example, oral, intravenous, intraperitoneal, intracerebral (intraparenchymal), intraventricular, intramuscular, intraocular, intraarterial, intraportal, or intralesional route; via sustained release systems or via implanted devices. In certain embodiments, the composition can be administered by bolus injection or by continuous infusion or by an implanted device.

The composition can also be administered topically via an implanted membrane, sponge, or another suitable material that absorbs or encapsulates the desired molecule. In certain embodiments, when an implanted device is used, the device can be implanted into any suitable tissue or organ, and the desired molecule can be delivered via diffusion, time-released bolus, or continuous administration.

It will be appreciated that any therapy can be performed by using the immunoconjugate of the present invention in place of or in addition to the anti-IL-23p19 antibody.

VIII. Methods and Compositions for Diagnosis and Detection

In certain embodiments, any of the anti-IL-23p19 antibodies or antigen-binding fragments thereof disclosed herein can be used to detect the presence of IL-23p19 in a biological sample. The term "detection" used herein includes quantitative and qualitative detections, and exemplary detections may involve immunohistochemistry, immunocytochemistry, flow cytometry (e.g., FACS), magnetic beads complexed with antibody molecules, ELISA, and PCR (e.g., RT-PCR). In certain embodiments, the biological sample is blood, serum, or other liquid samples of biological source. In certain embodiments, the biological sample includes cells or tissues. In some embodiments, the biological sample is derived from lesions related to immune system diseases (such as autoimmune diseases or inflammation).

In one embodiment, an anti-IL-23p19 antibody for use in a diagnostic or detection method is provided. In another aspect, a method for detecting the presence of IL-23p19 in a biological sample is provided. In certain embodiments, the method comprises detecting the presence of IL-23p19 protein in a biological sample. In certain embodiments, the IL-23p19 is human IL-23p19 or cynomolgus monkey IL-23p19. In certain embodiments, the method comprises contacting the biological sample with the anti-IL-23p19 antibody disclosed herein under a condition that allows the anti-IL-23p19 antibody to bind to IL-23p19, and detecting whether a complex is formed between the anti-IL-23p19 antibody and IL-23p19. The formation of the complex indicates the presence of IL-23p19. The method may be an in-vitro or in-vivo method. In one embodiment, the anti-IL-23p19 antibody is used to screen subjects suitable for treatment with the anti-IL-23p19 antibody, e.g., wherein IL-23p19 is the biomarker for screening.

In one embodiment, the antibody disclosed can be used to diagnose an IL-23 associated disease, e.g., an immune system disease (such as an autoimmune disease or inflammation), e.g., to evaluate (e.g., monitor) the response or progression, diagnosis and/or staging of a disease (an IL-23 associated disease, e.g., an immune system disease (such as an autoimmune disease or inflammation)) described herein in a subject. In certain embodiments, a labeled anti-IL-23p19 antibody is provided. The label includes, but is not limited to, a label or moiety (e.g., a fluorescent label, a chromophoric label, an electron-dense label, a chemiluminescent label, and a radioactive label) that is detected directly, and a moiety that is detected indirectly, such as an enzyme or a ligand, for example, by an enzymatic reaction or a molecular interaction. Exemplary labels include, but are not limited to, radioisotopes of $^{32}P$, $^{14}C$, $^{125}I$, $^{3}H$ and $^{131}I$, fluorophores (such as rare earth chelates or fluorescein) and derivatives thereof, rhodamine and derivatives thereof, dansyl, umbelliferone, luciferase (such as firefly luciferase and bacterial luciferase (U.S. Pat. No. 4,737,456)), fluorescein, 2,3-dihydrophthalazinedione, horseradish peroxidase (HR), alkaline phosphatase, 0-galactosidase, glucoamylase, lysozyme, carbohydrate oxidase (such as glucose oxidase, galactose oxidase and glucose-6-phosphate dehydrogenase), heterocyclic oxidase (such as uricase and xanthine oxidase), enzymes oxidizing dye precursors with hydrogen peroxide (such as HR, lactoperoxidase, or microperoxidase), biotin/avidin, spin labels, phage labels, stable free radicals, etc.

In some embodiments of the invention provided herein, the sample is obtained prior to the treatment with the anti-IL-23p19 antibody. In some embodiments, the sample is obtained prior to treatment with a medication for an IL-23 associated disease, e.g., an immune system disease (such as an autoimmune disease or inflammation). In some embodiments, the sample is a formalin-fixed, paraffin-embedded (FFPE) sample. In some embodiments, the sample is a biopsy (e.g., a core biopsy) specimen, a surgical specimen (e.g., a specimen from a surgical resection), or a fine-needle aspirate.

In some embodiments, IL-23p19 is detected prior to the treatment, e.g., prior to the initial treatment or prior to a treatment after an interval from a certain treatment.

In some embodiments, a method for treating an IL-23 associated disease, e.g., an immune system disease (such as an autoimmune disease or inflammation) is provided, wherein the method comprises: detecting the presence of IL-23p19 in a subject (e.g., a sample, such as a sample of the subject), thereby determining an IL-23p19 value; comparing the IL-23p19 value to a reference value; and administering to the subject a therapeutically effective amount of an anti-IL-23p19 antibody (e.g., the anti-IL-23p19 antibodies described herein) optionally in combination with one or more of other therapies if the IL-23p19 value is greater than the reference value, thereby treating the IL-23 associated disease, e.g., the immune system disease (such as the autoimmune disease or inflammation).

IX. Exemplary Anti-IL-23p19 Antibodies of the Present Invention

TABLE 1

Amino acid sequences of CDRs of exemplary antibodies of the present invention (determined according to Abm scheme)

| Antibody | HCDR1 | HCDR2 | HCDR3 | LCDR1 | LCDR2 | LCDR3 |
|---|---|---|---|---|---|---|
| 17D1 chimeric antibody | GYTFTSYLMH (SEQ ID NO: 1) | YINPYNDGTN (SEQ ID NO: 2) | NWDLPY (SEQ ID NO: 4) | RASQSISDYLH (SEQ ID NO: 5) | YASQSMS (SEQ ID NO: 6) | QNGHSFPFT (SEQ ID NO: 7) |
| 17D1 humamized antibody | GYTFTSYLMH (SEQ ID NO: 1) | YINPYNEGTN (SEQ ID NO: 3) | NWDLPY (SEQ ID NO: 4) | RASQSISDYLH (SEQ ID NO: 5) | YASQSMS (SEQ ID NO: 6) | QQGHSFPFT (SEQ ID NO: 8) |
| 17D1-Y TE | GYTFTSYLMH (SEQ ID NO: 1) | YINPYNEGTN (SEQ ID NO: 3) | NWDLPY (SEQ ID NO: 4) | RASQSISDYLH (SEQ ID NO: 5) | YASQSMS (SEQ ID NO: 6) | QQGHSFPFT (SEQ ID NO: 8) |
| Consensus sequence | SEQ ID NO: 1 | YINPYNXGTN (wherein X can be any amino acid preferably D or E) (SEQ ID NO: 23) | SEQ ID NO: 4 | SEQ ID NO: 5 | SEQ ID NO: 6 | QXGHSFPFT (wherein X can be any amino acid, preferably Q or N) (SEQ ID NO: 24) |

TABLE 2

Amino acid sequences of heavy chain and light chain variable regions of exemplary antibodies of the present invention

| Antibody | VH | VL |
|---|---|---|
| 17D1 chimeric antibody | EVQLQQSVPELVKPGASVKMSCKTSGYTFTSYLMHWVKQKPGQGLEWIGYINPYNDGTNYNEKFKGKATLTSDKSSSTAYMELSSLTSEDSAVYYCARNWDLPYWGQGTLVTVSA (SEQ ID NO: 9) | DIVMTQSPATLSVTPGDRVSLSCRASQSISDYLHWYQQKSHESPRLLIKYASQSMSGIPSRFSGSGSGSDFTLSINSVEPEDVGVYYCQNGHSFPFTFGAGTKLELK (SEQ ID NO: 11) |

TABLE 2-continued

Amino acid sequences of heavy chain and light chain variable regions of exemplary antibodies of the present invention

| Antibody | VH | VL |
|---|---|---|
| 17D1 humanized antibody | QVQLVQSGAEVKKPGASVKVSCKASGY TFTSYLMHWVRQAPGQGLEWMGYINPY NEGTNYAQKFQGRVTMTRDTSISTAYME LSRLRSDDTAVYYCARNWDLPYWGQGT LVTVSS(SEQ ID NO: 10) | DIQMTQSPSSLSASVGDRVTITCRASQSI SDYLHWYQQKPGKAPKLLIKYASQSMS GVPSRFSGSGSGSDFTLTISSLQPEDFAT YYCQQGHSFPFTFGQGTKLEIK(SEQ ID NO: 12) |
| 17D1 - YTE | QVQLVQSGAEVKKPGASVKVSCKASGY TFTSYLMHWVRQAPGQGLEWMGYINPY NEGTNYAQKFQGRVTMTRDTSISTAYME LSRLRSDDTAVYYCARNWDLPYWGQGT LVTVSS(SEQ ID NO: 10) | DIQMTQSPSSLSASVGDRVTITCRASQSI SDYLHWYQQKPGKAPKLLIKYASQSMS GVPSRFSGSGSGSDFTLTISSLQPEDFAT YYCQQGHSFPFTFGQGTKLEIK(SEQ ID NO: 12) |

TABLE 3

Amino acid sequences of heavy chains (HC) and light chains (LC) of exemplary antibodies of the present invention

| Antibody | HC | LC |
|---|---|---|
| 17D1 chimeric antibody | SEQ ID NO: 13 | SEQ ID NO: 16 |
| 17D1 humanized antibody | SEQ ID NO: 14 | SEQ ID NO: 17 |
| 17D1-YTE | SEQ ID NO: 15 | SEQ ID NO: 17 |

These and other aspects and embodiments of the present invention are illustrated in the drawings (brief description of the drawings follows) and in the following detailed description of the present invention and are described in the following examples. Any or all of the features described above and throughout the present invention may be combined in various embodiments of the present invention. The following examples further illustrate the present invention. However, it should be understood that the examples are described by way of illustration rather than limitation, and various modifications may be made by those skilled in the art.

EXAMPLES

Example 1. Preparation of Hybridoma Cells

This experiment adopted hybridoma techniques. Mice were immunized by a murine IL-12p40/human IL-23p19 fusion protein. Then splenocytes of the mice were obtained and fused with myeloma cells to give hybridoma cells capable of expressing target antibodies.

Hybridoma Fusion

TABLE 4

Experimental animals and immunological information

| Mouse | Balb/c (Beijing Vital River Laboratory Animal Technology Co., Ltd.) |
|---|---|
| Immunizing antigen | Fusion protein constructed with murine IL-12p40 and human IL-23p19 (prepared as follows) |
| Immunizing method | 50 µg/mouse, subcutaneous (SC), 50 µL per spot, 4 spots |
| Times of immunizing | 3 |
| Final booster immunization | 50 µg of murine IL-12p40/human IL-23p19 fusion protein, intraperitoneal injection (IP), 3 days before fusion |

Preparation of Murine IL-12p40/Human IL-23p19 Fusion Protein, Cynomolgus Monkey IL23 Protein, and Human IL23 Protein In order to screen for an antibody that only binds to human IL23p19, a murine IL-12p40/human IL-23p19 fusion protein was designed as follows: murine IL12 p40 (NCBI: P43432, Met23-Ser335) and human IL-23 p19 (NCBI: AAG37232, Ala21-Pro189) were linked by a linker (GSGSSRGGSGSGGSGGGGSKL) and a His tag (HHHHHH) was linked to the C terminus.

Design of cynomolgus monkey IL23 protein: cynomolgus monkey IL12p40 (NCBI: AEY84628, Ile23-Ser328) and cynomolgus monkey IL23p19 (NCBI: AEY84629, Ala21-Pro189) were linked by the linker (GSGSSRGGSGSGGSGGGGSKL) and a His tag (HHHHHH) was linked to the C terminus.

Design of human IL23 protein: human IL12p40 (NCBI: P29460, Ile23-Ser328) and human IL23p19 (NCBI: AAG37232, Ala21-Pro189) were linked by the linker (GSGSSRGGSGSGGSGGGGSKL) and a His tag (HHHHHH) was linked to the C terminus.

The proteins were expressed by Expi293 cells (Thermo, A14527) in large amount following the procedures for transient transfection kit ExpiFectamine™ 293 (Theomo, A14524). The supernatant was collected and purified on a HisTrap Excel (GE, 17-3712-06) pre-loaded column to a final purity >90%.

Preparation of Reference Antibody Guselkumab (Gmab)

The reference antibody guselkumab sequence was from WHO INN website (Jassen company guselkumab, hereinafter referred to as Gmab; for the amino acid sequence see also Patent No. US20160237151). The antibody was expressed by Expi293 cells (Thermo, A14527) in large amount following the procedures for transient transfection kit ExpiFectamine™ 293 (Theomo, A14524). The supernatant was collected and purified using HiTrap MabSelect SuRe (GE, 11003495) to a purity >95%.

Preparation of electroporation: dishes were thoroughly soaked with 70% ethanol and dried in an ultra clean bench for use.

Isolation of splenocytes: mice were sacrificed by cervical dislocation, sterilized with 75% alcohol for 5 min, and immediately placed on a mouse dissecting plate in the ultra clean bench in a left lateral decubitus position, with limbs fixed with No. 7 needles. The spleen was taken out after aseptically opening the abdominal cavity and then washed with basal medium (prepared as per the Table 5 below), and surrounding connective tissues were carefully removed. The spleen was then transferred to another dish containing the basal medium. The spleen was pressed with an elbow needle, perforated with a small needle, and then pressed with forceps to fully release the splenocytes so as to prepare a splenocyte suspension. After being filtered through a 70-μM cell strainer, the cell suspension was washed once by 30 mL of basal medium and centrifuged at 1200 rpm for 6 min.

TABLE 5

| Name | Composition | Preparation |
| --- | --- | --- |
| Basal medium | RPMI-1640 (Hyclone) | 90% |
|  | FBS (Hyclone) | 10% |
|  | GlutaMAX ™ Supplement (Gibco ) | 1× |

Lysis of erythrocytes: The supernatant was discarded and the cells were resuspended in 10 mL of RBC lysis buffer (GIBCO). Then 20 mL of RBC lysis buffer was added. The suspension was left to stand for 5 min and centrifuged at 1100 rpm for 6 min. After discarding the supernatant, the cells were resuspended in 10 mL of basal medium. Then 30 mL of basal medium was added, and the cells were centrifuged at 1100 rpm for 6 min. After discarding the supernatant, the cells were resuspended in 20 mL of basal medium and counted.

Electroporation: SP2/0 cells (mouse myeloma cells) (ATCC) were resuspended in 20 mL of basal medium and counted. SP2/0 cells and splenocytes with RBCs lysed were mixed in a ratio of 1:2 to 1:1, and centrifuged at 1000 rpm for 6 min. After discarding the supernatant, the mixed cells were resuspended in 10 mL of fusion buffer (BTXpress). Then 15 mL of fusion buffer was added, and the mixture was centrifuged at 1000 rpm for 5 min with the supernatant discarded. The above steps were repeated. The cells were resuspended in an appropriate volume of fusion buffer and the mixed cell density was adjusted to $1\times10^7$ cells/mL. The settings of the electroporation apparatus are shown in Table 6 below. 2 mL of the above cell suspension was added into each dish for electroporation.

TABLE 6

| Settings of electroporation apparatus | |
| --- | --- |
| Condition: | Mouse (SP2/0-ECF-F) |
| Alignment: | 60 v, 30 sec |
| Membrane breaking: | 1500 V, 30 μs, 3X |
| Post-fusion pulse: | 60 V, 3 sec |

Post-fusion plating: The cells were left in the dish at room temperature for 5 min. The cells were transferred to a centrifuge tube and diluted to $1-2\times10^4$ cells/mL with selective medium (prepared as per the Table 7 below). 100 μL of cell suspension was added to each well of a 96-well plate. The selective medium was refreshed 7 days after the fusion. After Day 10 of culture (or longer, depending on the cell growth), hybridoma cells were screened by ELISA for expressing antibodies that specifically bound to IL-23p19 and did not bind to IL-12p40.

TABLE 7

| Selective medium | | |
| --- | --- | --- |
| Name | Composition | Preparation |
| Selective medium | RPMI-1640 (Hyclone) | 90% |
|  | FBS (Hyclone) | 10% |
|  | HAT medium (Gibco) | 1× |
|  | GlutaMAX ™ Supplement (Gibco) | 1× |

Positive Hybridoma Cell Subcloning

Subcloning: 200 μL of the basal medium described above was added to each well in rows 2 to 8 of a 96-well plate. 300 μL of fused cells in positive wells were added to each well in the first row at a density of about $1\times10^5$ cells/mL. Using a multi-channel pipette, 100 μL of the cell suspension in row 1 was transferred into row 2, from which 100 μL was transferred into the next row after mixing. The above step was repeated until a mixture of 300 μL was obtained in the last row. After sitting for 15 min, the cells were counted under a microscope. A corresponding volume containing about 100 cells was added to 20 mL of basal medium for mixing and plating at 200 μL each well. After one week, the cells were observed under a microscope. Monoclonal wells were marked for screening positive wells.

Cell cryopreservation: The cells were monitored for their states. Those growing well with viability over 90% were centrifuged at 1000 rpm for 5 min and the supernatant was discarded. The cells were resuspended in cryoprotectant (45.5% of FBS (Hyclone), 44.5% of RPMI-1640 (Hyclone), 10% of DMSO) with a final concentration of $1\times10^7$ cells/mL, aliquoted into cryopreservation tubes, placed in programmed freezing containers, and cryopreserved at −80° C.

Example 2. Hybridoma Cell Screening Activity

This experiment adopted a functional design, in which the anti-IL-23p19 antibody inhibited IL-23 for inducing IL-17 secretion in mouse splenic lymphocytes, and hybridoma cells were screened for expressing anti-IL-23p19 antibody that inhibits IL-23-induced IL-17 secretion in mouse splenic lymphocytes.

Isolation of Mouse Splenic Lymphocytes

Blank Bal b/c mice (Beijing Vital River Laboratory Animal Technology Co., Ltd.) were sacrificed by cervical dislocation, and the spleens of the mice were taken and soaked in clean PBS buffer; the spleens were transferred into a cell strainer in a dish containing an appropriate amount of PBS buffer; the tissues were crushed using a clean syringe to dissociate cells inside the membrane, and the cells were suspended in the buffer in a dish after passing through the cell strainer; PBS containing mouse spleen lymphocytes was collected and centrifuged at 400 g for 10 min; the supernatant was discarded and 5 mL of red blood cell lysis buffer (ACK lysis buffer (GIBCO)) was added to resuspend the cells; after 2 min of lysing, the cells were centrifuged at 400 g for 10 min; the cells was washed once using 30 mL of PBS and centrifuged at 400 g, and the supernatant was discarded; 5 mL of complete medium (RPMI-1640 medium with 10% FBS) was added to prepare a cell suspension.

Plating

10 μL of the cell suspension obtained above was subjected to cell counting, and the cells were diluted to a density of $4\times10^6$ cells/mL with complete medium. Then the cells were transferred into a 96-well plate at 100 μL per well, with a total number achieving $4\times10^5$ cells per well.

IL-23 or Mixture of IL-23 and Hybridoma Supernatant Induced IL-17 Secretion in Mouse Splenocytes IL-23 (R&D Systems, Catalog No. 1290-IL-500/CF) was diluted to 120 ng/mL with complete medium. 120 μL of the IL-23 was mixed with 120 μL of the hybridoma cell culture supernatant obtained in Example 1, and then incubated at 37° C. for 30 min; after 30 min, 100 μL of the mixture was added to mouse spleen lymphocytes plated on the 96-well plate which had been coated with mouse spleen lymphocytes, then mixed well and incubated at 37° C. for 4 days; a mixture of 120 μL of IL-23 and 120 μL of complete medium (RPMI-1640 medium with 10% FBS) was used as the negative control.

Determination of IL-17 Content and Calculation of the Inhibition Rate of Hybridoma Supernatant In the present invention, the IL-17 content was detected by the Mouse IL-17 DuoSet ELISA kit (R&D Systems, Catalog No. DY421), and the calculation formula of the inhibition rate of hybridoma supernatant is:

$$\text{Inhibition}(\%) = (\text{IL-17}_{negative\ control} - \text{IL-17}_{test\ sample}) / \text{IL-17}_{negative\ control} \times 100\%$$

By such functional experiment a hybridoma cell with activity superior to the reference antibody was found, with the clone number being 17D1. Results are shown in Table 8 below:

TABLE 8

|  | IL-17 (pg/mL) | Inhibition (%) |
|---|---|---|
| 17D1 | 118 | 94 |
| Gmab | 286 | 86 |
| Negative control | 2055 | 0 |

Example 3. Preparation of Chimeric Antibody

Using molecular biotech, the antibody sequence of the anti-IL-23p19 antibody produced by the hybridoma cells in Example 1 was obtained and was used to construct a human-mouse chimeric antibody.

Hybridoma Sequencing

RNA extraction: about $5 \times 10^6$ cells of freshly cultured 17D1 clone were centrifuged at 300 g for 5 min, and the supernatant was discarded. 500 μL of LY buffer (Biomiga) (20 μL of betamercaptoethanol per 1 mL prior to use) was added to the precipitate, and was shaken until being clear. The mixture was transferred into a centrifugation tube and centrifuged at 13000 rpm for 2 min. The flow-through was collected. 100% ethanol was added to the flow-through in a ratio of 1/2, and the fluid was mixed upside down 5 times until being clear. The clear solution was added to an RNA collection tube and centrifuged at 13000 rpm for 1 min, and the supernatant was discard. 500 μL of RB (Recovery Buffer) (Takara) was added, and the mixture was centrifuged at 13000 rpm for 30 s, and was centrifuged for another 30 s after adding 500 μL of RNA washing buffer (Biomiga) (an appropriate amount of ethanol was added before use). The above procedures were repeated before further centrifugation and an evaporation for a complete removal of ethanol. The collection column (from PrimeScript II 1st Strand cDNA Synthesis Kit) was pre-treated with 30 μL of DEPC-treated water, and the mixture was centrifuged at 12000 g for 2 min and the eluents were collected. The RNA concentration was measured.

Reverse transcription was performed by using Prime-Script II 1st Strand cDNA Synthesis Kit (Takara) to obtain cDNA, the steps are as follows (the mentioned reagents were from this kit): Preparation reaction system I is shown in Table 9 below.

TABLE 9

| Name | Amount |
|---|---|
| Oligo dT Primer | 1 μL |
| dNTP | 1 μL |
| Template RNA (RNA obtained above) | 5 ug |
| RNase free ddH$_2$O | Make up to 10 μL |

After incubation at 65° C. for 5 min, the system was rapidly cooled on ice. The reaction system I was added to the following reverse transcription system (Table 10) in a total amount of 20 μL.

TABLE 10

| Reverse transcription system | |
|---|---|
| Name | Amount |
| Reaction system I | 10 μL |
| 5× PrimeScript II Buffer | 4 μL |
| RNase Inhibitor (40 U/μL) | 0.5 μL (20 U) |
| PrimeScript II RTase (200 U/μL) | 1 μL (200 U) |
| RNase free ddH$_2$O | Make up to 20 μL |

After slowly mixing, reverse transcription was induced in the following conditions of 42° C. for 60 min→95° C. for 5 min. The mixture was then cooled on ice before cDNA collection. The cDNA was linked to the T vector using Mighty TA-cloning Kit (Takara): The heavy chain variable region and light chain variable region were amplified separately through PCR, and the PCR reaction system is shown in Table 11 below.

TABLE 11

| Name | Amount |
|---|---|
| TaKaRa EX Taq HS | 0.25 μL |
| Primer Mix 1 (Table 1 below) | 1 μL |
| Primer Mix 2 (Table 2 below) | 1 μL |
| cDNA (obtained as mentioned above) | 1 μL |
| 10× Ex Taq buffer | 5 μL |
| dNTP Mixture (2.5 mM each) | 4 μL |
| RNase free ddH$_2$O | Make up to 50 μL |

PCR reaction conditions are shown in Table 12.

TABLE 12

| 94° C. | 5 min | |
| 94° C. | 30 s | 30 cycles |
| 55° C. | 30 s | |
| 72° C. | 60 s | |
| 72° C. | 5 min | |

0.5 μL of pMD20-T vector (Takara) and 5 μL of Ligation Mighty Mix (Takara) were added to 4.5 μL of the PCR product from the above PCR reaction. The mixture was gently mixed, and incubated at 37° C. for 2 h to give a ligation product.

Transformation of Cells:

TOP10 competent cells (Tiangen Biotech (Beijing) Co., Ltd.) were taken from −80° C. and thawed on ice. 5 μL of the ligation product obtained above was added to the thawed TOP10 competent cells. The mixture was mixed well and then incubated on ice for 30 min. After heat shock at 42° C.

for 90 s, the obtained mixture was rapidly cooled on ice for 2 min. 900 μL of LB culture medium (Sangon Biotech (Shanghai) Co., Ltd.) was added to the EP tube, and the mixture was incubated at 37° C. on a shaker at 220 rpm for 1 h. The cells were centrifuged at 3000 g for 2 min. 800 μL of supernatant was discarded, and the cells were resuspended in the remaining medium for coating an ampicillin plate. The cells were incubated overnight at 37° C. Clones were separated for sequencing.

Construction of Chimeric Antibody

The VH and VL regions, which had been sequenced, of the anti-IL-23p19 antibody generated from the hybridoma of Example 1 were amplified by PCR: the sequences of forward and reverse primers are shown in Tables 13 and 14.

TABLE 13

Primer (Primer Mix 1) for heavy chain variable region (VH) of mouse anti-IL-23p19 antibody

| Primer | Sequence (5'-3') | Ratio (%) |
|---|---|---|
| OVH1 | SAGGTCCAGCTGCAGCAGYYTGG | 28.6 |
| OVH2 | CAGGTRCAGCTGAAGSAGTCAGG | 10.7 |
| OVH3 | GAKGTGCAGCTTCAGCAGTCRGG | 8.9 |
| OVH5 | GAVGTGAWGCTGGTGGAGTCTGR | 7.1 |
| OVH11 | GAAGTGCAGCTGTTGGAGACTGG | 3.6 |
| OVH14 | GAGGTTCAGCTGCAGCAGTCTGK | 16.1 |
| OVH15 | CAGGTTCACCTACAACAGTCTGG | 3.5 |
| REVESE-6 | CTGAGGARACGGTGACCG | 6 |
| REVESE-4 | CTGAGGAGACTGTGAGAGWGGT | 4 |
| REVESE-2-1 | CTGAGGAGACGGTGACTGAGGT | 2 |
| REVESE-2-2 | CTGCAGAGACAGTGACCAGAGT | 2 |
| Water | | q.s. |

After components were mixed in above proportions, the resulting Primer Mix 1 was used for subsequent VH PCR amplification.

TABLE 14

Primer (Primer Mix 2) for light chain variable region (VL) of mouse anti-IL-23p19 antibody

| Primer | Sequence (5'-3') | Ratio (%) |
|---|---|---|
| IGKV1 | GATGYTKTGATGACCCAAACTCCA | 17.65 |
| IGKV2-109 | GATATTGTGATGACGCAGGCTGCA | 5.88 |
| IGKV2-112 | GATATTGTGATAACCCAGGATGAA | 5.88 |
| IGKV3-7 | GACATTGTGCTAACACAGTCTCCT | 2.94 |
| IGKV3-1-5.10 | RACATTGTGCTSACCCAATCTCCA | 29.41 |
| IGKV5-48 | GACATCTTGCTGACTCAGTCTCCA | 2.94 |
| IGKV6-13 | GACATTGTGATGACCCAGTCTCAA | 2.94 |
| IGKV6-32 | AGTATTGTGATGACCCAGACTCCC | 2.94 |
| IGKV14 | GACATCMAGATGACMCAGTCTCCA | 11.76 |
| IGKV4-51.86 | GAAAATGTGCTCACYCAGTCTCCA | 2.94 |

TABLE 14-continued

Primer (Primer Mix 2) for light chain variable region (VL) of mouse anti-IL-23p19 antibody

| Primer | Sequence (5'-3') | Ratio (%) |
|---|---|---|
| IGKV7-33 | GACATTGTGATGACTCAGTCTCCA | 2.94 |
| IGKV9-123 | GACATCCAGATGATTCAGTCTCCA | 2.94 |
| IGKV9-124 | GACATCCAGATGACCCAGTCTCCA | 2.94 |
| IGKV10-95 | GATATCCAGATGACACAGACTACT | 2.94 |
| IGKV11-125 | GATGTCCAGATGATTCAGTCTCCA | 2.94 |
| mK-Rev | TACAGTTGGTGCAGCATCAG | |

After components were mixed in proportions, the resulting Primer Mix 2 was used for subsequent VL PCR amplification.

The PCR system is shown in Table 15.

TABLE 15

| Name | Amount |
|---|---|
| 2× Prime STAR HS (Premix) | 25 μL |
| Primer Mix* | 2 μL |
| Plasmid template | 0.5 μL |
| dNTP Mixture (2.5 mM each) | 4 μL |
| RNase free ddH$_2$O | Make up to 50 μL |

*For VH amplification, the Primer Mix 1 was used; for VL amplification, the Primer Mix 2 was used.

The gel was cut to recover the PCR amplification products.

Homologous Recombination:

The homologous recombination system is shown in Table 16 below.

TABLE 16

| Name | Amount |
|---|---|
| Recovering fragments | 1 μL |
| pTT5 vector | 2 μL |
| 5× Buffer (Takara) | 2 μL |
| Homologous recombination enzyme (Takara) | 1 μL |
| ddH$_2$O | Make up to 10 μL |

After incubation for 30 min at 37° C., a recombinant product was obtained. The TOP10 competent cells were transformed by the recombinant product, and monoclones were separated for sequencing. Clones containing plasmids with correct insertion directions were selected as positive clones, and preserved.

The amino acid sequences of the CDRs, light and heavy chain variable regions, light and heavy chains of one exemplary chimeric antibody (17D1 chimeric antibody) disclosed herein, as well as the corresponding nucleic acid sequences are listed in Tables 1-3 herein and sequence listing section.

Example 4. Humanization of Chimeric Antibody

The chimeric antibody obtained in Example 3 was humanized. Humanization was performed via the following steps:
1) determining the structure of CDR loops;
2) searching a human germline sequence database for closest homologous sequences for each V/J region of the heavy and light chains;

3) screening the human germlines for highest match in heavy and light chains and minimum amount of back mutation;
4) constructing the CDRs of the chimeric antibody onto the framework of a human antibody;
5) determining the positions of amino acids that maintained the CDR functions in the framework based on the sequences and structural features;
6) adding back mutation (back to the input amino acids) at important positions identified; and
7) optimizing amino acids at risk sites.

The amino acid sequences of the CDR, light and heavy chain variable regions, light and heavy chains of one exemplary chimeric antibody (17D1 humanized antibody) disclosed herein, as well as the corresponding nucleic acid sequences are listed in Tables 1-3 herein and sequence listing section.

Example 5. Expression and Purification of Humanized Antibody

The humanized antibody of the present invention was expressed in CHO-S cells and was purified. According to the manufacturer's instructions, the Freedom® CHO-S® kit (Invitrogen) was used to prepare antibody-expressing CHO-S cells. The DNA sequences of the heavy and light chains of the 17D1 humanized antibody molecule were first inserted into the same pCHO1.0 plasmid, with the heavy chain being upstream of the light chain. The constructed pCHO1.0 plasmids were then transferred into CHO cells (Life Technology) by chemical transfection and electrotransfection, and the antibody yield was measured by ForteBio to determine the transfection efficiency after 48 h of transfection. The transfected cells were subjected to two cycles of pressurized filtration to give a cell pool of high antibody expression. The cells were then expanded to express a large quantity of antibodies, and the cell supernatant was collected and purified by Protein A affinity chromatography to a purity of >95%.

Preparation of YTE Antibody

Site-directed mutations (M252Y/S254T/T256E) were introduced at 3 positions of the Fc segment of 17D1 humanized antibody to enhance the binding capacity to human FcRn, in order to extend its half-life in vivo. Similar to the preparation of 17D1 humanized antibody, Freedom® CHO-S® kit (Invitrogen) was used to prepare antibody-expressing CHO-S cells. The transfected cells were subjected to two cycles of pressurized filtration to give a cell pool of high antibody expression. The cells were then expanded to express a large quantity of antibodies, and the cell supernatant was collected and purified by Protein A affinity chromatography to a purity of >95%. The obtained antibody was named 17D1-YTE.

Example 6. Affinity Assay of Humanized Antibodies

The equilibrium dissociation constant ($K_D$) of the above 17D1 humanized antibody and 17D1-YTE of the present invention to human IL-23p19 was measured by biological optical interferometry (ForteBio).

The ForteBio affinity assay was performed according to the prior art (Estep, P., et al., High throughput solution based measurement of antibody-antigen affinity and epitope binning. *MAbs*, 2013.5(2): p. 270-8). Briefly, the sensor was equilibrated offline in an assay buffer for 30 min, and was equilibrated online for 60 s to establish a baseline. The purified antibodies obtained as described above were loaded online onto an AHQ sensor (ForteBio) for the ForteBio affinity assay. The sensor with the loaded antibodies was then exposed to 100 nM XX antigens for 5 min before transferring the sensor to the assay buffer for 5 min of dissociation to measure the dissociation rate.

The kinetic analysis was performed using a 1:1 binding model.

In the assay described above, the affinity of the above 17D1 humanized antibody 17D1-YTE of the present invention and the reference antibody Gmab to human IL-23 (obtained as described in Example 1, 100 mM) is shown in Table 17 below.

TABLE 17

Affinity of antibodies to human IL-23

| Sample | KD (M) | kon (1/Ms) | koff (1/s) | Response |
|---|---|---|---|---|
| 17D1 humanized antibody | 1.75E−09 | 9.37E+04 | 1.64E−04 | 0.3168 |
| 17D1-YTE | 6.11E−10 | 9.31E+04 | 5.69E−05 | 0.3058 |
| Gmab | 1.04E−09 | 1.15E+05 | 1.20E−04 | 0.4096 |

From results of Table 17 above, it was noted that the above 17D1 humanized antibody and 17D1-YTE of the present invention demonstrated extremely high affinity. 17D1 had similar affinity with the reference antibody Gmab, and 17D1-YTE had higher affinity than the reference antibody Gmab.

The equilibrium dissociation constant ($K_D$) for binding of the above 17D1 humanized antibody and 17D1-YTE antibody of the present invention to human interleukin protein human IL-12 (ACRO Biosystems, Cat #IL2-H4210) or human IL-12p40 (ACRO Biosystems, Cat #NK2-H52H7) of the same family was measured by biological optical interferometry (ForteBio) (Table 18).

TABLE 18

Affinity of antibodies to different human antigens

| Sample | Analyte | KD (M) | kon(1/Ms) | koff(1/s) |
|---|---|---|---|---|
| 17D1-YTE | Human IL-12 | No binding | | |
| 17D1-YTE | Human IL-12p40 | No binding | | |
| 17D1 humanized antibody | Human IL-12 | No binding | | |
| 17D1 humanized antibody | Human IL-12p40 | No binding | | |

Results in Table 18 above indicated that neither 17D1 humanized antibody nor 17D1-YTE antibody binds to human IL-12, human IL-12p40.

The equilibrium dissociation constant ($K_D$) for binding of the above 17D1 humanized antibody and 17D1-YTE of the present invention to cynomolgus monkey IL-23 (obtained as described in Example 1, 100 mM) was measured by biological optical interferometry (ForteBio) (Table 19).

TABLE 19

Affinity of 17D1-YTE to cynomolgus monkey IL-23

| Sample | KD (M) | Kon (1/Ms) | Koff (1/s) | Response |
|---|---|---|---|---|
| 17D1 humanized antibody | 1.67E−09 | 5.04E+04 | 8.44E−05 | 0.2152 |
| 17D1-YTE | 3.70E−10 | 5.84E+04 | 2.16E−05 | 0.2067 |
| Gmab | 9.41E−10 | 6.16E+04 | 5.80E−05 | 0.2838 |

From the figures and tables above, it was noted that the above 17D1 humanized antibody and 17D1-YTE of the present invention have extremely high affinity, and 17D1-YTE is similar to the reference antibody Gmab in affinity.

ForteBio Affinity Assay of Candidate Antibodies to Human FcRn

In this assay, the ForteBio Octet RED96 System was used to detect the kinetic constant ($K_D$) for binding of 17D1 humanized antibody and 17D1-YTE to human FcRn (Acro, Catalog No. FCM-H5286). The results are shown in Table 20. The affinity of 17D1-YTE to human FcRn was three times those of 17D1 humanized antibody and reference antibody Gmab.

First, the 17D1 humanized antibody, 17D1-YTE, and Gmab (guselkumab) prepared as described above were labeled with biotin, with the molar ratio of antibody to biotin being 1:3. The biotin was removed using a desalting column and the labeled samples were re-measured and stored for later use.

An appropriate amount of SA sensor (Fortebio, Catalog No. 18-5019) was soaked in the analysis buffer for 30 min. The biotinylated 17D1 humanized antibody, 17D1-YTE, and Gmab were diluted to 100 nM, and human FcRn (Acro, Catalog No. FCM-H5286) was serially two-fold diluted to 5 concentrations (5, 2.5, 1.25, 0.625, 0.3125 µg/mL). The sensor was first equilibrated in the analysis buffer for 120 s. Then the biotinylated antibodies were loaded on the SA sensor for 100 s of immobilization, and the sensor was equilibrated for another 120 s after immobilization. After the baseline was stabilized, the serially diluted FcRns binded to the sensors with the same antibody immobilization level. After 100 s for binding, the sensors were equilibrated in analysis buffer for 120 s to measure the binding and dissociation. The experimental data were analyzed using a 1:1 model. The affinity data are shown in Table 20.

TABLE 20

Affinity of 17D1-YTE to human FcRn

| Sample | KD (M) | Kon (1/Ms) | Koff (1/s) | Response |
|---|---|---|---|---|
| 17D1 humanized antibody | 1.23E−08 | 1.15E+06 | 1.41E−02 | 0.5656 |
| 17D1-YTE | 3.34E−09 | 9.88E+05 | 3.30E−03 | 0.7699 |
| Gmab | 1.32E−08 | 1.12E+06 | 1.48E−02 | 0.5317 |

Example 7. Activity Characterization of Humanized Antibodies

A functional experiment was designed to determine the activity of the 17D1 humanized antibody and 17D1-YTE obtained above to inhibit IL-23-induced IL-17 secretion in mouse splenic lymphocytes. The assay method is same as Example 2, except that 4 µg/mL PBS solutions of 17D1 humanized antibody and 17D1-YTE were used, with Gmab being the reference. The results are shown in FIG. 1.

In the above assay, 17D1 humanized antibody and 17D1-YTE inhibited IL-23 for inducing IL-17 secretion in mouse spleen lymphocytes, which were similar as compared with the reference antibody.

Example 8. Pharmacodynamics in Animals

In this experiment, C57BL/6 male mice were used to determine the prophylactic anti-inflammatory effect of the IL-23 antibodies disclosed herein.

Figure 2:
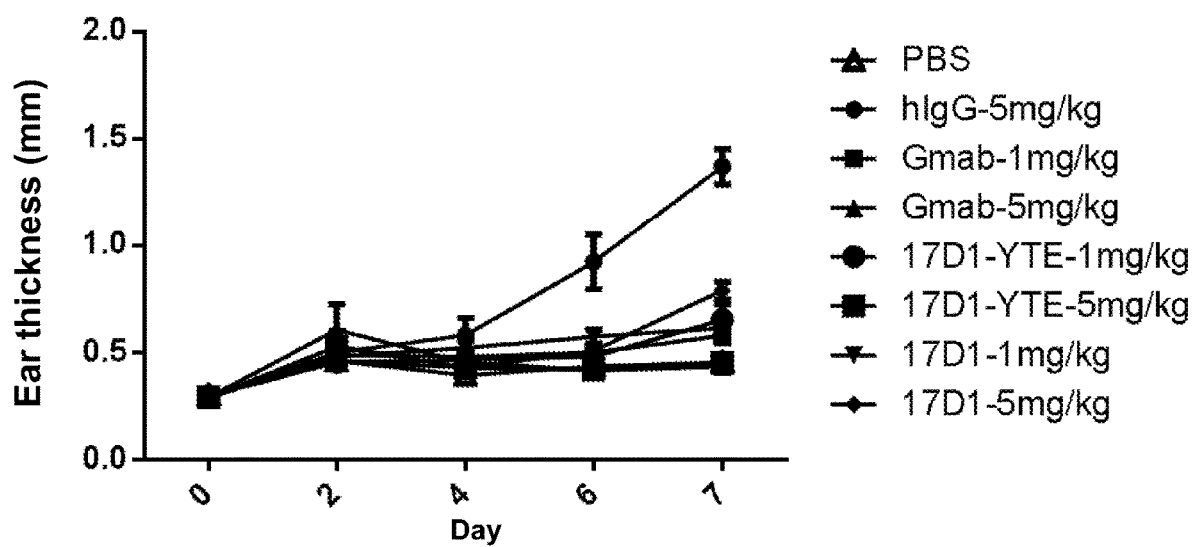
FIG. 2 shows changes in mean right ear thickness of mice over time by group.

C57BL/6 male mice: C57Bl/6 male mice (42-62 days) were purchased from Beijing Vital River Laboratory Animal Technology Co., Ltd. The 48 mice were SPF grade, with certificate No. 11400700260631. After arrival, the mice had been acclimated for 7 days before the start of experiment. Administration: A total of 48 mice were randomized into 8 groups with 6 mice in each group (a male mouse in the h-IgG+PBS group was beaten and was seriously injured, thus being removed from the group). PBS solution of antibody was injected intraperitoneally one day in advance at the following doses: h-IgG-5 mg/kg; 17D1 humanized antibody (hereinafter referred to as 17D1)-1 mg/kg; 17D1-5 mg/kg; 17D1-YTE-1 mg/kg; 17D1-YTE-5 mg/kg; Gmab-1 mg/kg; Gmab-5 mg/kg. From the next day, PBS was injected subcutaneously at the right ear of the first group h-IgG-5 mg/kg and IL-23 antigen (in PBS) at 1 µg per mouse was injected subcutaneously at the right ear of remaining groups (human IL-23 protein obtained as described in Example 1) for 9 days. The dosage and route of administration are shown in Table 21. The thickness and weight of the right ear of the mice were monitored every 1-2 days, until the end of Day 9. The thickness of the right ear of the mouse was measured with a vernier caliper (FIG. 2). The mice were weighted using an electronic balance.

TABLE 21

Experiment design

| Group | Route of administration | Group | Route of administration |
|---|---|---|---|
| h-IgG-5 mg/kg | Intraperitoneal | PBS | Subcutaneous injection at right ear |
| h-IgG-5 mg/kg | Intraperitoneal | IL-23(1 ug) | Subcutaneous injection at right ear |
| 17D1-1 mg/kg | Intraperitoneal | IL-23(1 ug) | Subcutaneous injection at right ear |
| 17D1-5 mg/kg | Intraperitoneal | IL-23(1 ug) | Subcutaneous injection at right ear |
| 17D1-YTE-1 mg/kg | Intraperitoneal | IL-23(1 ug) | Subcutaneous injection at right ear |
| 17D1-YTE-5 mg/kg | Intraperitoneal | IL-23(1 ug) | Subcutaneous injection at right ear |
| Gmab-1 mg/kg | Intraperitoneal | IL-23(1 ug) | Subcutaneous injection at right ear |
| Gmab-5 mg/kg | Intraperitoneal | IL-23(1 ug) | Subcutaneous infection at right ear |

*Antibodies were administered intraperitoneally one day in advance; IL-23 antigen was injected subcutaneously at the right ear for 9 consecutive days.

TABLE 22

Drug information

| Name | Batch number | Origin | Strength or concentration |
| --- | --- | --- | --- |
| 17D1 humanized antibody | 20170927 | Prepared and purified as described in Example 5 | 21.5 mg/mL |
| 17D1-YTE | 20171010 | Prepared and purified as described in Example 5 | 23.1 mg/mL |
| Gmab | 20170803 | Prepared and purified as described in Example 1 | 7.3 mg/mL |
| Human IL-23 protein | 20161206 | Prepared and purified as described in Example 1 | 1 mg/mL |
| h-IgG | 160308-02 | Equitech-Bio | 1 g/vial, formulated with PBS to 10 mg/mL |

Figure 3:
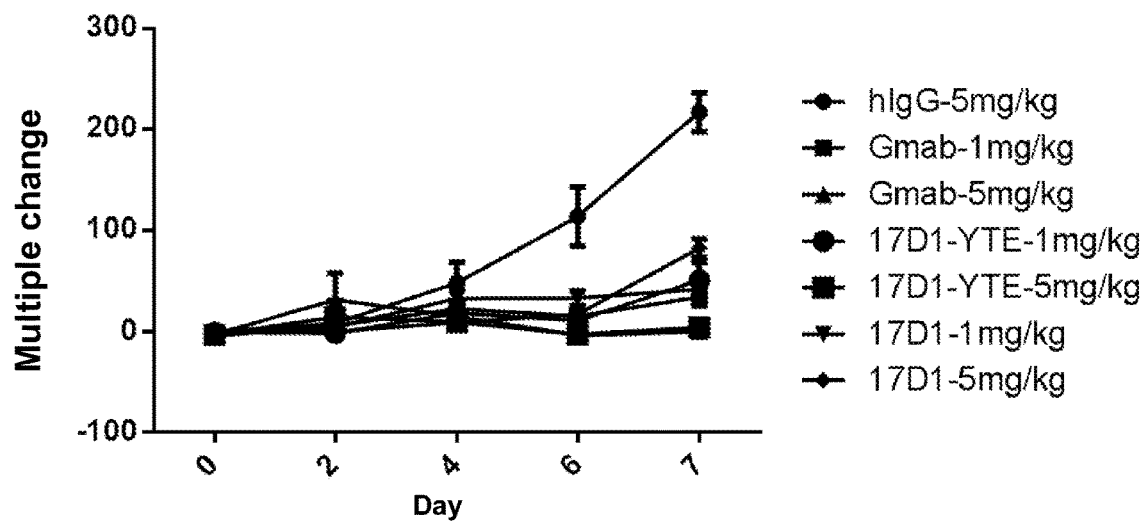
FIG. 3 shows changes in ear swelling inhibition rate of mice over time by group.
Figure 4:
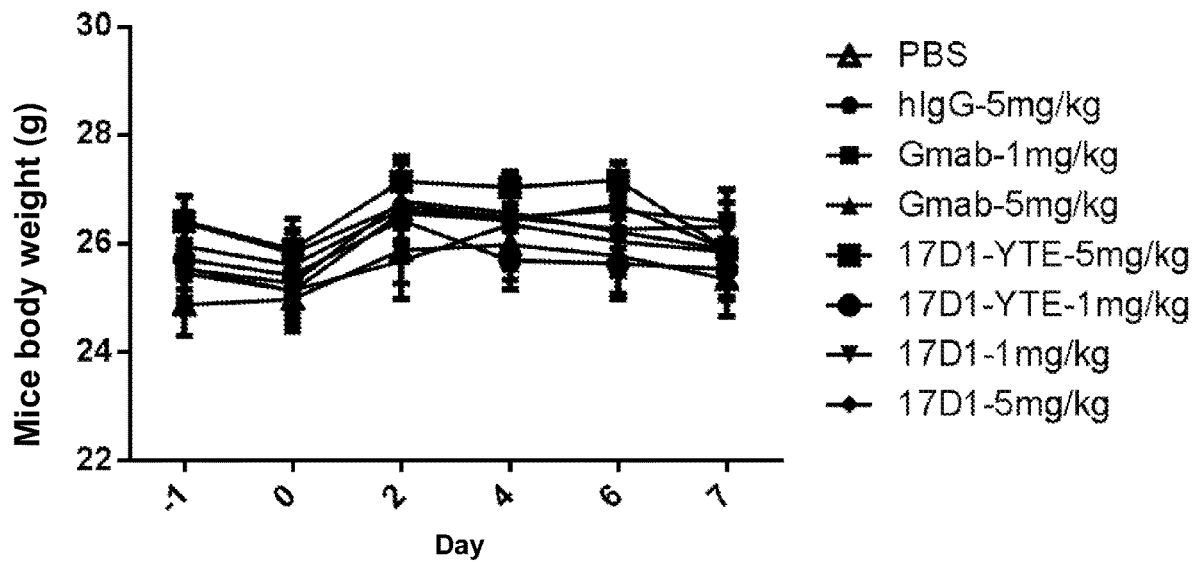
FIG. 4 shows changes in body weight of mice over time by group.

The ear swelling inhibition rate is shown in FIG. 3: After 7 days of subcutaneous injection of IL-23 antigen at the right ear, all of 17D1-1 mg/kg, 17D1-5 mg/kg, 17D1-YTE-1 mg/kg, 17D1-YTE-5 mg/kg, Gmab-1 mg/kg and Gmab-5 mg/kg had good effects on ear swelling inhibition; as compared with H-IgG, the swelling inhibition rate was 71%, 54%, 67%, 86%, 74%, and 88% for 17D1-1 mg/kg, 17D1-5 mg/kg, 17D1-YTE-1 mg/kg, 17D1-YTE-5 mg/kg, Gmab-1 mg/kg, and Gmab-5 mg/kg. Meanwhile, the body weight of the mice was monitored. As shown in FIG. 4, there was no significant difference in body weight of mice. Therefore, the IL-23 antibodies in this study have significant preventive anti-inflammatory effects.

TABLE 23

Ear swelling inhibition on Day 7 (%)

| Group | Ear thickness (mm) | Ear swelling inhibition rate (%) |
| --- | --- | --- |
| h-IgG-5 mg/kg (IL-23) | 1.368 | N/A |
| 17D1-1 mg/kg (IL-23) | 0.612 | 71% |
| 17D1-5 mg/kg (IL-23) | 0.787 | 54% |
| 17D1-YTE-1 mg/kg (IL-23) | 0.650 | 67% |
| 17D1-YTE-5 mg/kg (IL-23) | 0.448 | 86% |
| Gmab-1 mg/kg(IL-23) | 0.518 | 74% |
| Gmab-5 mg/kg(IL-23) | 0.432 | 88% |

TGI %=100%*(ear thickness in control group−ear thickness in treatment group)/(ear thickness in control group−post-administration ear thickness in control group)

wherein the post-administration ear thickness in the control group was 0.298 mm.

The invention claimed is:

1. An antibody or an antigen-binding fragment thereof that binds to IL-23p19, comprising three complementarity determining regions of a heavy chain variable region (HCDR1, HCDR2, and HCDR3), and three complementarity determining regions of a light chain variable region (LCDR1, LCDR2, and LCDR3), wherein
HCDR1 comprises the amino acid sequence set forth in SEQ ID NO: 1, HCDR2 comprises the amino acid sequence set forth in SEQ ID NO: 2, 3, or 23, HCDR3 comprises the amino acid sequence set forth in SEQ ID NO: 4, LCDR1 comprises the amino acid sequence set forth in SEQ ID NO: 5, LCDR2 comprises the amino acid sequence set forth in SEQ ID NO: 6, and LCDR3 comprises the amino acid sequence set forth in SEQ ID NO: 7, 8, or 24.

2. The antibody or antigen-binding fragment thereof according to claim 1, comprising a heavy chain variable region and/or a light chain variable region, wherein
(i) the heavy chain variable region comprises: three complementarity determining regions (HCDR1, HCDR2, and HCDR3) comprising the amino acid sequences set forth in SEQ ID NOs: 1, 3, and 4, respectively; and
the light chain variable region comprises: three complementarity determining regions (LCDR1, LCDR2, and LCDR3) comprising the amino acid sequences set forth in SEQ ID NOs: 5, 6, and 8, respectively; or
(ii) the heavy chain variable region comprises three complementarity determining regions (HCDR1, HCDR2, and HCDR3) comprising the amino acid sequence set forth in SEQ ID NOs: 1, 2, and 4, respectively;
and
the light chain variable region comprises three complementarity determining regions (LCDR1, LCDR2, and LCDR3) comprising the amino acid sequences set forth in SEQ ID NOs: 5, 6, and 7, respectively; or
iii) the heavy chain variable region comprises three complementarity determining regions (HCDR1, HCDR2, and HCDR3) comprising the amino acid sequences set forth in SEQ ID NOs: 1, 23, and 4, respectively;
and
the light chain variable region comprises three complementarity determining regions (LCDR1, LCDR2, and LCDR3) comprising the amino acid sequences set forth in SEQ ID NOs: 5, 6, and 24, respectively.

3. The antibody or the antigen-binding fragment thereof according to claim 1, comprising a light chain variable region and/or a heavy chain variable region, wherein
(i) the heavy chain variable region comprises an amino acid sequence having at least 90% identity to the amino acid sequence set forth in SEQ ID NO: 10; and
the light chain variable region comprises an amino acid sequence having at least 90% identity to the amino acid sequence set forth in SEQ ID NO: 12; or
(ii) the heavy chain variable region comprises an amino acid sequence having at least 90% identity to the amino acid sequence set forth in SEQ ID NO: 9; and
the light chain variable region comprises an amino acid sequence having at least 90% identity to the amino acid sequence set forth in SEQ ID NO: 11.

4. The antibody or the antigen-binding fragment thereof according to claim 1, wherein
(i) the heavy chain variable region comprises the amino acid sequence set forth in SEQ ID NO: 10, and the light chain variable region comprises the amino acid sequence set forth in SEQ ID NO: 12; or
(ii) the heavy chain variable region comprises the amino acid sequence set forth in SEQ ID NO: 9, and the light chain variable region comprises the amino acid sequence set forth in SEQ ID NO: 11.

5. The antibody or the antigen-binding fragment thereof according to claim 1, wherein
(a) the heavy chain comprises an amino acid sequence having at least 85% identity to the amino acid sequence set forth in SEQ ID NO: 15;
and
the light chain comprises an amino acid sequence having at least 85% identity to the amino acid sequence set forth in SEQ ID NO: 17;
or
(b) the heavy chain comprises an amino acid sequence having at least 85% identity to the amino acid sequence set forth in SEQ ID NO: 14;
and
the light chain comprises an amino acid sequence having at least 85% identity to the amino acid sequence set forth in SEQ ID NO: 17; or
(c) the heavy chain comprises an amino acid sequence having at least 85% identity to the amino acid sequence set forth in SEQ ID NO: 13;
and
the light chain comprises an amino acid sequence having at least 85% identity to the amino acid sequence set forth in SEQ ID NO: 16.

6. The antibody or antigen-binding fragment thereof according to claim 1, wherein
(a) the heavy chain comprises the amino acid sequence set forth in SEQ ID NO: 15; and
the light chain comprises the amino acid sequence set forth in SEQ ID NO: 17; or
(b) the heavy chain comprises the amino acid sequence set forth in SEQ ID NO: 14; and
the light chain comprises the amino acid sequence set forth in SEQ ID NO: 17; or
(c) the heavy chain comprises the amino acid sequence set forth in SEQ ID NO: 13; and the light chain comprises the amino acid sequence set forth in SEQ ID NO: 16.

7. The antibody or the antigen-binding fragment thereof according to claim 1, wherein the antibody is an antibody in the form of IgG1, IgG2, or IgG4, or an antigen-binding fragment thereof.

8. The antibody or the antigen-binding fragment thereof according to claim 1, wherein the antibody is a monoclonal antibody.

9. The antibody or an antigen-binding fragment thereof according to claim 1, wherein the antibody is a humanized antibody, a human antibody, or a chimeric antibody.

10. The antibody or the antigen-binding fragment thereof according to claim 1, wherein the antigen-binding fragment is an antibody fragment selected from the group consisting of Fab, Fab', Fab'-SH, Fv, single-chain antibody, (Fab')$_2$, diabody (dAb), and linear antibody.

11. The antibody or the antigen-binding fragment thereof according to claim 1, wherein the antibody is a bispecific or multispecific antibody molecule.

12. The antibody or antigen-binding fragment thereof according to claim 11, wherein the bispecific antibody binds to (i) IL-23p19, and (ii) TNFα, IL-17A, or IL-17F.

13. An isolated nucleic acid encoding the antibody or the antigen-binding fragment thereof of claim 1.

14. An expression vector comprising the nucleic acid of claim 13.

15. A host cell comprising the nucleic acid according to claim 13.

16. A method for preparing an antibody or an antigen-binding fragment thereof that binds to IL-23p19, the method comprising: cultivating a host cell in conditions suitable for expressing a nucleic acid encoding the antibody or the antigen-binding fragment thereof according to claim 1, and optionally, isolating the antibody or the antigen-binding fragment thereof.

17. An immunoconjugate, comprising the antibody or the antigen-binding fragment thereof according to claim 1, an additional substance.

18. A pharmaceutical composition, comprising the antibody or the antigen-binding fragment thereof according to claim 1, and optionally one or more additional therapeutic agents.

19. A combination product, comprising the antibody or the antigen-binding fragment thereof according to claim 1, and one or more additional therapeutic agents selected from the group consisting of chemotherapeutic agents, cytokines, cytotoxic agents, other antibodies, small molecule drugs, and immunomodulatory agents.

20. A method for mediating antibody-dependent cellular cytotoxicity (ADCC) or activating effector T cells or NF-κB signaling pathway or eliminating regulatory T cells in a subject, the method comprising administering to the subject an effective amount of the antibody or the antigen-binding fragment thereof according to claim 1.

21. A method for preventing or treating IL-23 associated disease in a subject, the method comprising administering to the subject an effective amount of the antibody or the antigen-binding fragment thereof according to claim 1.

22. The method according to claim 21, further comprising administering to the subject one or more combined therapies selected from the group consisting of a treatment modality and/or an additional therapeutic agent.

23. The method according to claim 22, wherein the treatment modality comprises surgical treatment and/or radiation therapy, or wherein the additional therapeutic agent comprises a chemotherapeutic agent, a cytokine, a cytotoxic agent, an additional antibody, a small molecule drug, or an immunomodulatory agent.

24. The method according to claim 23, wherein the immunomodulatory agent is an anti-inflammatory agent or an immunosuppressant.

25. The method according to claim 21, wherein the IL-23 associated disease is an immune system disease.

26. The method according to claim 21, wherein the IL-23 associated disease is inflammatory bowel disease, rheumatoid arthritis, ankylosing spondylitis, systemic lupus erythematosus, scleroderma, Sjogren's syndrome, multiple sclerosis, inflammation, asthma, idiopathic thrombocytopenic purpura, psoriatic arthritis, or Crohn's disease.

27. The method according to claim 21, wherein the IL-23 associated disease is ulcerative colitis or psoriasis.

* * * * *

```
SEQUENCE LISTING

<160> NUMBER OF SEQ ID NOS: 25

<210> SEQ ID NO 1
<211> LENGTH: 10
<212> TYPE: PRT
<213> ORGANISM: Artificial
<220> FEATURE:
<223> OTHER INFORMATION: 17D1 antibody HCDR1

<400> SEQUENCE: 1

Gly Tyr Thr Phe Thr Ser Tyr Leu Met His
1               5                   10

<210> SEQ ID NO 2
<211> LENGTH: 10
<212> TYPE: PRT
<213> ORGANISM: Artificial
<220> FEATURE:
<223> OTHER INFORMATION: 17D1 chimeric antibody HCDR2

<400> SEQUENCE: 2

Tyr Ile Asn Pro Tyr Asn Asp Gly Thr Asn
1               5                   10

<210> SEQ ID NO 3
<211> LENGTH: 10
<212> TYPE: PRT
<213> ORGANISM: Artificial
<220> FEATURE:
<223> OTHER INFORMATION: 17D1 humanized antibody or 17D1-YTE antibody
      HCDR2

<400> SEQUENCE: 3

Tyr Ile Asn Pro Tyr Asn Glu Gly Thr Asn
1               5                   10

<210> SEQ ID NO 4
<211> LENGTH: 6
<212> TYPE: PRT
<213> ORGANISM: Artificial
```

```
<220> FEATURE:
<223> OTHER INFORMATION: 17D1 antibody HCDR3

<400> SEQUENCE: 4

Asn Trp Asp Leu Pro Tyr
1               5

<210> SEQ ID NO 5
<211> LENGTH: 11
<212> TYPE: PRT
<213> ORGANISM: Artificial
<220> FEATURE:
<223> OTHER INFORMATION: 17D1 antibody LCDR1

<400> SEQUENCE: 5

Arg Ala Ser Gln Ser Ile Ser Asp Tyr Leu His
1               5                   10

<210> SEQ ID NO 6
<211> LENGTH: 7
<212> TYPE: PRT
<213> ORGANISM: Artificial
<220> FEATURE:
<223> OTHER INFORMATION: 17D1 antibody LCDR2

<400> SEQUENCE: 6

Tyr Ala Ser Gln Ser Met Ser
1               5

<210> SEQ ID NO 7
<211> LENGTH: 9
<212> TYPE: PRT
<213> ORGANISM: Artificial
<220> FEATURE:
<223> OTHER INFORMATION: 17D1 chimeric antibody LCDR3

<400> SEQUENCE: 7

Gln Asn Gly His Ser Phe Pro Phe Thr
1               5

<210> SEQ ID NO 8
<211> LENGTH: 9
<212> TYPE: PRT
<213> ORGANISM: Artificial
<220> FEATURE:
<223> OTHER INFORMATION: 17D1 humanized antibody or 17D1-YTE antibody
      HCDR3

<400> SEQUENCE: 8

Gln Gln Gly His Ser Phe Pro Phe Thr
1               5

<210> SEQ ID NO 9
<211> LENGTH: 115
<212> TYPE: PRT
<213> ORGANISM: Artificial
<220> FEATURE:
<223> OTHER INFORMATION: 17D1 chimeric antibody VH

<400> SEQUENCE: 9

Glu Val Gln Leu Gln Gln Ser Val Pro Glu Leu Val Lys Pro Gly Ala
1               5                   10                  15

Ser Val Lys Met Ser Cys Lys Thr Ser Gly Tyr Thr Phe Thr Ser Tyr
            20                  25                  30

Leu Met His Trp Val Lys Gln Lys Pro Gly Gln Gly Leu Glu Trp Ile
        35                  40                  45
```

Gly Tyr Ile Asn Pro Tyr Asn Asp Gly Thr Asn Tyr Asn Glu Lys Phe
            50                  55                  60

Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Asn Trp Asp Leu Pro Tyr Trp Gly Gln Gly Thr Leu Val Thr
            100                 105                 110

Val Ser Ala
        115

<210> SEQ ID NO 10
<211> LENGTH: 115
<212> TYPE: PRT
<213> ORGANISM: Artificial
<220> FEATURE:
<223> OTHER INFORMATION: 17D1 humanized antibody or 17D1-YTE antibody VH

<400> SEQUENCE: 10

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Leu Met His Trp Val Arg Gln Ala Pro Gly Gln Gly Leu Glu Trp Met
             35                  40                  45

Gly Tyr Ile Asn Pro Tyr Asn Glu Gly Thr Asn Tyr Ala Gln Lys Phe
            50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asn Trp Asp Leu Pro Tyr Trp Gly Gln Gly Thr Leu Val Thr
            100                 105                 110

Val Ser Ser
        115

<210> SEQ ID NO 11
<211> LENGTH: 107
<212> TYPE: PRT
<213> ORGANISM: Artificial
<220> FEATURE:
<223> OTHER INFORMATION: 17D1 chimeric antibody VL

<400> SEQUENCE: 11

Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
             35                  40                  45

Lys Tyr Ala Ser Gln Ser Met Ser Gly Ile Pro Ser Arg Phe Ser Gly
         50                  55                  60

Ser Gly Ser Gly Ser Asp Phe Thr Leu Ser Ile Asn Ser Val Glu Pro
 65                  70                  75                  80

-continued

Glu Asp Val Gly Val Tyr Tyr Cys Gln Asn Gly His Ser Phe Pro Phe
                85                  90                  95

Thr Phe Gly Ala Gly Thr Lys Leu Glu Leu Lys
            100                 105

<210> SEQ ID NO 12
<211> LENGTH: 107
<212> TYPE: PRT
<213> ORGANISM: Artificial
<220> FEATURE:
<223> OTHER INFORMATION: 17D1 humanized antibody or 17D1-YTE antibody VL

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu His Trp Tyr Gln Gln Lys Pro Gly Lys Ala Pro Lys Leu Leu Ile
        35                  40                  45

Lys Tyr Ala Ser Gln Ser Met Ser Gly Val Pro Ser Arg Phe Ser Gly
    50                  55                  60

Ser Gly Ser Gly Ser Asp Phe Thr Leu Thr Ile Ser Ser Leu Gln Pro
65                  70                  75                  80

Glu Asp Phe Ala Thr Tyr Tyr Cys Gln Gln Gly His Ser Phe Pro Phe
                85                  90                  95

Thr Phe Gly Gln Gly Thr Lys Leu Glu Ile Lys
            100                 105

<210> SEQ ID NO 13
<211> LENGTH: 445
<212> TYPE: PRT
<213> ORGANISM: Artificial
<220> FEATURE:
<223> OTHER INFORMATION: 17D1 chimeric antibody HC

<400> SEQUENCE: 13

Glu Val Gln Leu Gln Gln Ser Val Pro Glu Leu Val Lys Pro Gly Ala
1               5                   10                  15

Ser Val Lys Met Ser Cys Lys Thr Ser Gly Tyr Thr Phe Thr Ser Tyr
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Trp Asp Leu Pro Tyr Trp Gly Gln Gly Thr Leu Val Thr
            100                 105                 110

Val Ser Ala Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

-continued

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 14
<211> LENGTH: 444
<212> TYPE: PRT
<213> ORGANISM: Artificial
<220> FEATURE:
<223> OTHER INFORMATION: 17D1 humanized antibody HC

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Leu Met His Trp Val Arg Gln Ala Pro Gly Gln Gly Leu Glu Trp Met
            35                  40                  45

Gly Tyr Ile Asn Pro Tyr Asn Glu Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

```
Met Glu Leu Ser Arg Leu Arg Ser Asp Asp Thr Ala Val Tyr Tyr Cys
                85                  90                  95

Ala Arg Asn Trp Asp Leu Pro Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 15
<211> LENGTH: 444
<212> TYPE: PRT
<213> ORGANISM: Artificial
<220> FEATURE:
<223> OTHER INFORMATION: 17D1-YTE antibody HC
```

<400> SEQUENCE: 15

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Leu Met His Trp Val Arg Gln Ala Pro Gly Gln Gly Leu Glu Trp Met
        35                  40                  45
Gly Tyr Ile Asn Pro Tyr Asn Glu Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Asn Trp Asp Leu Pro Tyr Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Tyr Ile Thr Arg Glu Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
```

```
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 16
<211> LENGTH: 214
<212> TYPE: PRT
<213> ORGANISM: Artificial
<220> FEATURE:
<223> OTHER INFORMATION: 17D1-chimeric antibody LC

<400> SEQUENCE: 16

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Met Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 214
<212> TYPE: PRT
<213> ORGANISM: Artificial
<220> FEATURE:
<223> OTHER INFORMATION: 17D1-humanized antibody or 17D1-YTE antibody LC

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30
```

Leu His Trp Tyr Gln Gln Lys Pro Gly Lys Ala Pro Lys Leu Leu Ile
                35                  40                  45

Lys Tyr Ala Ser Gln Ser Met Ser Gly Val Pro Ser Arg Phe Ser Gly
     50                  55                  60

Ser Gly Ser Gly Ser Asp Phe Thr Leu Thr Ile Ser Ser Leu Gln Pro
 65                  70                  75                  80

Glu Asp Phe Ala Thr Tyr Tyr Cys Gln Gln Gly His Ser Phe Pro Phe
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 1339
<212> TYPE: DNA
<213> ORGANISM: Artificial
<220> FEATURE:
<223> OTHER INFORMATION: 17D1 chimeric antibody HC DNA

<400> SEQUENCE: 18
gaggttcagc tgcagcagtc tgtacctgag ctggtaaagc ctggggcttc agtgaagatg     60
tcctgcaaga cttctggata cacattcact agttatctta tgcactgggt gaagcagaag    120
cctgggcagg gccttgagtg gattggatat attaatcctt acaatgatgg tactaactac    180
aatgagaagt tcaaaggcaa ggccacactg acttcagaca atcctccag cacagcctac     240 atggagctca gcagcctgac ctctgaggac tctgcggtct attactgtgc aagaaactgg    300 gacctcccctt actggggcca aggactctg gtcactgtct ctgcaggcct ccaccaaagg    360
ccccagcgtc ttcccctgg ctcctagctc caaatccacc agcggcggca ccgctgctct     420
gggctgcctg gtgaaagatt acttccccga gcctgtgacc gtgtcctgga cagcggcgc    480 tctgacaagc ggcgtgcaca ccttcccgc tgtcctccaa tcctccggac tgtactccct    540
gagctccgtg gtgaccgtgc ccagctcctc cctcggaacc cagacataca tctgcaacgt    600
gaaccacaag ccttccaaca ccaaggtgga caagaaggtg agcctaagt cctgcgacaa     660 aacccacacc tgtcccccctt gtcctgctcc cgagctcctg gaggacctt ccgtgttcct     720 cttccctccc aaacccaagg acaccctgat gattagcagg acacccgagg tgacctgtgt    780
ggtggtggat gtgagccatg aggaccccga ggtgaagttt aactggtacg tggacggcgt    840
cgaggtgcac aacgctaaga ccaaacccag ggaggagcag tacaactcca catacccggt    900
cgtgagcgtg ctgaccgtcc tgcaccagga ttggctgaat ggcaaggagt acaagtgcaa    960

```
ggtgagcaac aaggccctgc ccgcccccat cgagaagacc atcagcaagg ccaaaggaca    1020
gcctcgggag ccccaggttt atactctccc ccccagccgg gacgaactga ccaagaatca    1080
ggtgtccctc acctgcctcg tgaagggctt ttaccccagc gacattgccg tggagtggga    1140
gagcaatgga cagcccgaaa acaactacaa gaccacaccc cccgtcctgg actccgatgg    1200
cagcttcttc ctgtacagca agctgaccgt ggacaagagc aggtggcagc agggcaacgt    1260
gtttagctgc agcgtcatgc acgaggctct ccacaaccac tacacccaga agtccctgag    1320
cctgagcccc ggaaagtga                                                 1339

<210> SEQ ID NO 19
<211> LENGTH: 1335
<212> TYPE: DNA
<213> ORGANISM: Artificial
<220> FEATURE:
<223> OTHER INFORMATION: 17D1 humanized antibody HC DNA

<400> SEQUENCE: 19
caggtgcagc tggtgcagtc cggagctgag gtcaagaaac ccggcgcctc cgtgaaggtg      60
agctgcaagg ccagcggcta cacattcacc agctatctga tgcactgggt caggcaggcc     120
cctggacaag gcctggagtg gatgggctac atcaacccct acaacgaggg cacaaactac     180
gcccagaagt tccagggcag ggtgaccatg acccgggaca cctccatctc caccgcctat     240
atggagctct ccaggctgag gagcgatgac accgccgtgt attactgtgc caggaactgg     300
gacctgccct actggggaca gggcacactc gtgaccgtga gcagcgcttc caccaagggc     360
cctagcgtct ttcccctggc cccttccagc aagagcacca gcggaggcac cgctgctctc     420
ggctgtctcg tgaaggacta cttccccgag cctgtgaccg tgtcctggaa cagcggcgct     480
ctgacaagcg gcgtgcatac cttccccgcc gtgctgcagt cctccggact gtacagcctg     540
agctccgtgg tgacagtgcc tagcagcagc ctgggcaccc agacctacat ctgcaacgtc     600
aaccacaaac cctccaacac caaggtggac aagaaggtgg agcctaagtc ctgcgataag     660
acccacacct gccctccctg ccctgctcct gaactgctgg gcggaccttc cgtgttcctg     720
ttccccccca aacccaagga taccctgatg atctcccgga cccccgaggt gacatgcgtg     780
gtcgtcgacg tgtcccacga ggaccctgag gtgaagttca actggtacgt ggatggcgtg     840
gaggtgcaca cgccaagac aaagcccagg gaggagcagt acaactccac ctaccgggtg     900
gtgagcgtgc tgaccgtgct gcaccaggat tggctgaacg gcaaggaata taagtgcaag     960
gtgtccaaca aagccctgcc cgcccccatc gaaaagacaa tctccaaggc caagggccag    1020
cctcgggaac ctcaggtgta tacc ctgccc cctcccggg acgagctgac aaaaaaccag    1080
gtgtccctca cctgtctggt gaagggcttc tacccctccg atatcgctgt cgagtgggag    1140
tccaacggcc agcccgagaa caattataaa accacccccc ctgtgctgga ttccgacggc    1200
tccttcttcc tctactccaa gctgaccgtg gacaaatccc ggtggcagca gggaaacgtc    1260
ttctcctgct ccgtcatgca tgaggctctg cacaaccact acacccagaa gagcctgagc    1320
ctgagccccg atga                                                     1335

<210> SEQ ID NO 20
<211> LENGTH: 1335
<212> TYPE: DNA
<213> ORGANISM: Artificial
<220> FEATURE:
<223> OTHER INFORMATION: 17D1-YTE antibody HC DNA
```

<400> SEQUENCE: 20

| | | | |
|---|---|---|---|
| caggtgcagc tggtgcagtc cggagctgag gtcaagaaac ccggcgcctc cgtgaaggtg | 60 |
| agctgcaagg ccagcggcta cacattcacc agctatctga tgcactgggt caggcaggcc | 120 |
| cctggacaag gcctggagtg gatgggctac atcaaccctt acaacgaggg cacaaactac | 180 |
| gcccagaagt tccagggcag ggtgaccatg acccgggaca cctccatctc caccgcctat | 240 |
| atggagctct ccaggctgag gagcgatgac accgccgtgt attactgtgc caggaactgg | 300 |
| gacctgccct actggggaca gggcacactc gtgaccgtga gcagcgcttc caccaagggc | 360 |
| cctagcgtct tccccctggc cccttccagc aagagcacca gcggaggcac cgctgctctc | 420 |
| ggctgtctcg tgaaggacta cttccccgag cctgtgaccg tgtcctggaa cagcggcgct | 480 |
| ctgacaagcg gcgtgcatac cttccccgcc gtgctgcagt cctccggact gtacagcctg | 540 |
| agctccgtgg tgacagtgcc tagcagcagc ctgggcaccc agacctacat ctgcaacgtc | 600 |
| aaccacaaac cctccaacac caaggtggac aagaaggtgg agcctaagtc ctgcgataag | 660 |
| acccacacct gcccctccctg ccctgctcct gaactgctgg gcggaccttc cgtgttcctg | 720 |
| ttcccccca aacccaagga taccctgtac atcacccggg agcccgaggt gacatgcgtg | 780 |
| gtcgtcgacg tgtcccacga ggaccctgag gtgaagttca actggtacgt ggatggcgtg | 840 |
| gaggtgcaca acgccaagac aaagcccagg gaggagcagt acaactccac ctaccgggtg | 900 |
| gtgagcgtgc tgaccgtgct gcaccaggat tggctgaacg gcaaggaata taagtgcaag | 960 |
| gtgtccaaca aagccctgcc cgcccccatc gaaaagacaa tctccaaggc caagggccag | 1020 |
| cctcgggaac ctcaggtgta taccctgccc ccctcccggg acgagctgac aaaaaaccag | 1080 |
| gtgtccctca cctgtctggt gaagggcttc taccctccg atatcgctgt cgagtgggag | 1140 |
| tccaacggcc agcccgagaa caattataaa accaccccc ctgtgctgga ttccgacggc | 1200 |
| tccttcttcc tctactccaa gctgaccgtg gacaaatccc ggtggcagca gggaaacgtc | 1260 |
| ttctcctgct ccgtcatgca tgaggctctg cacaaccact acacccagaa gagcctgagc | 1320 |
| ctgagccccg gatga | 1335 |

<210> SEQ ID NO 21
<211> LENGTH: 646
<212> TYPE: DNA
<213> ORGANISM: Artificial
<220> FEATURE:
<223> OTHER INFORMATION: 17D1 chimeric antibody LC DNA

<400> SEQUENCE: 21

| | | | |
|---|---|---|---|
| gacattgtga tgactcagtc tccagccacc ctgtctgtga ctccaggaga tagagtctct | 60 |
| ctttcctgca gggccagcca gagtattagc gactacttac actggtatca acaaaaatca | 120 |
| catgagtctc caaggcttct catcaaatat gcttcccaat ccatgtctgg gatcccctcc | 180 |
| aggttcagtg gcagtggatc agggtcagat ttcactctca gtatcaacag tgtggaacct | 240 |
| gaagatgttg gagtgtatta ttgtcaaaat ggtcacagtt ttccgttcac gttcggtgct | 300 |
| gggaccaagc tggagctgaa accggaccgt ggccgcccct ccgtgttca tctttccccc | 360 |
| ctccgacgag cagctgaagt ccggaaccgc cagcgtggtg tgcctcctga caacttttta | 420 |
| cccccgggag gccaaggtgc agtggaaggt ggacaacgcc ctgcaaagcg gcaactccca | 480 |

```
ggaatccgtc accgagcagg attccaagga ttccacctac agcctgtcct ccaccctgac    540
actgtccaag gccgactacg agaagcacaa ggtgtacgcc tgcgaggtga cacaccaggg    600
cctgagcagc cccgtgacca agtccttcaa ccggggcgag tgttga                  646

<210> SEQ ID NO 22
<211> LENGTH: 645
<212> TYPE: DNA
<213> ORGANISM: Artificial
<220> FEATURE:
<223> OTHER INFORMATION: 17D1 humanized antibody or 17D1-YTE antibody LC
      DNA

<400> SEQUENCE: 22
gacatccaga tgacccagag ccccagctcc ctgagcgctt ccgtcggaga tagggtgacc    60
atcacctgca gggcttccca gtccatcagc gactacctgc actggtacca gcaaaagcct   120
ggcaaggccc ccaagctgct catcaaatac gcctcccagt ccatgagcgg cgtgcctagc   180
aggttttccg gcagcggctc cggctccgac tttaccctga ccatctcctc cctgcagccc   240
gaggacttcg ccacctacta ctgccagcag ggccactcct tccccttcac cttcggccag   300
ggcaccaagc tcgagatcaa gaggaccgtg gccgcccct ccgtgttcat cttccccccc   360
tccgatgagc agctgaaatc cggaaccgcc agcgtggtgt gcctgctgaa caacttctac   420
cctcgggagg ccaaggtgca gtggaaggtg gacaacgccc tgcagtccgg caacagccag   480
gagtccgtga ccgagcagga cagcaaggac tccaccctact ccctgtccag caccctcaca   540
ctgtccaagg ccgactacga gaagcacaag gtgtacgcct gcgaggtgac acaccaggga   600
ctgagctccc ccgtgaccaa gagcttcaat aggggcgagt gctga                   645

<210> SEQ ID NO 23
<211> LENGTH: 10
<212> TYPE: PRT
<213> ORGANISM: Artificial
<220> FEATURE:
<221> NAME/KEY: misc_feature
<222> LOCATION: (7)..(7)
<223> OTHER INFORMATION: Antibody HCDR2, wherein Xaa can be any amino
      acid, preferably D or E

<400> SEQUENCE: 23

Tyr Ile Asn Pro Tyr Asn Xaa Gly Thr Asn
1               5                   10

<210> SEQ ID NO 24
<211> LENGTH: 9
<212> TYPE: PRT
<213> ORGANISM: Artificial
<220> FEATURE:
<221> NAME/KEY: misc_feature
<222> LOCATION: (2)..(2)
<223> OTHER INFORMATION: Antibody LCDR3, wherein Xaa can be any amino
      acid, preferably Q or N

<400> SEQUENCE: 24

Gln Xaa Gly His Ser Phe Pro Phe Thr
1               5

<210> SEQ ID NO 25
<211> LENGTH: 20
<212> TYPE: PRT
<213> ORGANISM: Artificial
<220> FEATURE:
<223> OTHER INFORMATION: Signal peptide sequence
```

```
<400> SEQUENCE: 25

Met Glu Thr Asp Thr Leu Leu Leu Trp Val Leu Leu Leu Trp Val Pro
1               5                   10                  15

Gly Ser Thr Gly
            20
```